(12) United States Patent
Altshuler et al.

(10) Patent No.: US 7,540,869 B2
(45) Date of Patent: Jun. 2, 2009

(54) METHOD AND APPARATUS FOR IMPROVED VASCULAR RELATED TREATMENT

(75) Inventors: Gregory B. Altshuler, Wilmington, MA (US); Michael Z. Smirnov, St. Petersburg (RU)

(73) Assignee: Palomar Medical Technologies, Inc., Burlington, MA (US)

( * ) Notice: Subject to any disclaimer, the term of this patent is extended or adjusted under 35 U.S.C. 154(b) by 48 days.

(21) Appl. No.: 10/331,134

(22) Filed: Dec. 27, 2002

(65) Prior Publication Data

US 2004/0010298 A1    Jan. 15, 2004

Related U.S. Application Data

(60) Provisional application No. 60/343,811, filed on Dec. 27, 2001.

(51) Int. Cl.
*A61B 18/18* (2006.01)
(52) U.S. Cl. ............... 606/9; 606/3; 607/88; 128/898
(58) Field of Classification Search ............ 606/3, 606/7–9, 15; 607/88–92, 94; 128/898
See application file for complete search history.

(56) References Cited

U.S. PATENT DOCUMENTS

| 1,706,161 | A | 3/1929 | Hollnagel |
| 2,472,385 | A | 6/1949 | Rollman |
| 3,327,712 | A | 6/1967 | Kaufman et al. |
| 3,486,070 | A | 12/1969 | Engel |
| 3,527,932 | A | 9/1970 | Thomas |
| 3,538,919 | A | 11/1970 | Meyer |
| 3,597,652 | A | 8/1971 | Gates, Jr. |
| 3,622,743 | A | 11/1971 | Muncheryan |

(Continued)

FOREIGN PATENT DOCUMENTS

AT    400305 B    4/1995

(Continued)

OTHER PUBLICATIONS

Altshuler et al., "Acoustic response of hard dental tissues to pulsed laser action," SPIE, vol. 2080, Dental Application of Lasers, pp. 97-103, 1993.

(Continued)

*Primary Examiner*—Ahmed M Farah
(74) *Attorney, Agent, or Firm*—Thomas J. Engellenner; Deborah A. Miller; Nutter McClennen & Fish, LLP

(57) ABSTRACT

Methods and apparatus are provided for selectively heating blood vessels in a patients skin to effect a desired dermatological (medical or cosmetic) treatment. For shallow vessels, particularly plexus vessels and superficial vessels/veins, radiation is applied to the vessels involved in the treatment which includes substantial radiation in a blue band of approximately 380-450 nm. The invention also involves maximizing the radiation used for which the safety radio for the area being treated is greater then one and minimizing the radiation used for which the safety ratio is less then one. This generally involves, depending on the blood vessel involved in the treatment and the patient's skin type, using radiation in one or more of a blue, green-yellow and near infrared wavelength band and filtering out radiation at other wavelengths, including radiation between the wavelength bands used.

40 Claims, 15 Drawing Sheets

U.S. PATENT DOCUMENTS

| | | |
|---|---|---|
| 3,693,623 A | 9/1972 | Harte et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,900,034 A | 8/1975 | Katz et al. |
| 4,233,493 A | 11/1980 | Nath |
| 4,273,109 A | 6/1981 | Enderby |
| 4,275,335 A | 6/1981 | Ishida |
| 4,316,467 A | 2/1982 | Muckerheide |
| 4,388,924 A | 6/1983 | Weissman et al. |
| 4,456,872 A | 6/1984 | Froeschle |
| 4,461,294 A | 7/1984 | Baron |
| 4,524,289 A | 6/1985 | Hammond et al. |
| 4,539,987 A | 9/1985 | Nath et al. |
| 4,561,440 A | 12/1985 | Kubo et al. |
| 4,591,762 A | 5/1986 | Nakamura |
| 4,608,978 A | 9/1986 | Rohr |
| 4,617,926 A | 10/1986 | Sutton |
| 4,695,697 A | 9/1987 | Kosa |
| 4,718,416 A | 1/1988 | Nanaumi |
| 4,733,660 A | 3/1988 | Itzkan |
| 4,745,909 A | 5/1988 | Pelton et al. |
| 4,747,660 A | 5/1988 | Nishioka et al. |
| 4,749,913 A | 6/1988 | Stuermer et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,884,560 A | 12/1989 | Kuracina |
| 4,905,690 A | 3/1990 | Ohshiro et al. |
| 4,917,084 A | 4/1990 | Sinofsky |
| 4,926,227 A | 5/1990 | Jensen |
| 4,928,038 A | 5/1990 | Nerone |
| 4,930,504 A * | 6/1990 | Diamantopoulos et al. .... 607/88 |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,127,395 A | 7/1992 | Bontemps |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,267,399 A | 12/1993 | Johnston |
| 5,282,797 A | 2/1994 | Chess |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,342,358 A | 8/1994 | Daikuzono |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,358,503 A | 10/1994 | Bertwell et al. |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,458,140 A | 10/1995 | Eppstein et al. |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles |
| 5,531,739 A | 7/1996 | Trelles |
| 5,531,740 A | 7/1996 | Black |
| 5,549,660 A | 8/1996 | Mendes et al. |
| 5,558,667 A | 9/1996 | Yarborough et al. |
| 5,571,098 A * | 11/1996 | Domankevitz et al. ........ 606/15 |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,655,547 A | 8/1997 | Karni |
| 5,658,148 A | 8/1997 | Neuberger et al. |
| 5,658,323 A | 8/1997 | Miller |
| 5,660,836 A | 8/1997 | Knowlton |
| 5,662,643 A | 9/1997 | Kung et al. |
| 5,662,644 A | 9/1997 | Swor |
| 5,683,380 A * | 11/1997 | Eckhouse et al. .............. 606/9 |
| 5,698,866 A | 12/1997 | Doiron et al. |
| 5,707,403 A | 1/1998 | Grove et al. |
| 5,720,772 A | 2/1998 | Eckhouse |
| 5,722,397 A | 3/1998 | Eppstein |
| 5,735,844 A * | 4/1998 | Anderson et al. .............. 606/9 |
| 5,735,884 A | 4/1998 | Thompson et al. |
| 5,742,392 A | 4/1998 | Anderson et al. |
| 5,743,901 A | 4/1998 | Grove et al. |
| 5,755,751 A * | 5/1998 | Eckhouse .................... 607/88 |
| 5,759,200 A | 6/1998 | Azar |
| 5,769,076 A | 6/1998 | Mackawa et al. |
| 5,782,249 A | 7/1998 | Weber et al. |
| 5,810,801 A | 9/1998 | Anderson et al. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,827,264 A | 10/1998 | Hohla |
| 5,828,803 A | 10/1998 | Eckhouse |
| 5,830,208 A * | 11/1998 | Muller ........................ 606/9 |
| 5,836,877 A | 11/1998 | Zavislan |
| 5,836,999 A | 11/1998 | Eckhouse et al. |
| 5,840,048 A | 11/1998 | Cheng |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,871,480 A | 2/1999 | Tankovich |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,913,883 A | 6/1999 | Alexander et al. |
| 5,916,211 A | 6/1999 | Quon et al. |
| 5,944,748 A | 8/1999 | Mager et al. |
| 5,948,011 A | 9/1999 | Knowlton |
| 5,949,222 A | 9/1999 | Buono |
| 5,954,710 A | 9/1999 | Paolini et al. |
| 5,955,490 A | 9/1999 | Kennedy et al. |
| 5,964,749 A | 10/1999 | Eckhouse et al. |
| 5,968,033 A | 10/1999 | Fuller |
| 5,968,034 A | 10/1999 | Fullmer et al. |

| | | | | | | |
|---|---|---|---|---|---|---|
| 5,977,723 | A | 11/1999 | Yoon | 6,517,532 B1 | 2/2003 | Altshuler et al. |
| 5,984,915 | A | 11/1999 | Loeb et al. | 6,530,915 B1 | 3/2003 | Eppstein et al. |
| 6,015,404 | A | 1/2000 | Altshuler et al. | 6,537,270 B1 | 3/2003 | Elbrecht et al. |
| 6,022,316 | A | 2/2000 | Epstein et al. | 6,558,372 B1 | 5/2003 | Altshuler |
| 6,026,828 | A | 2/2000 | Altshuler | 6,572,637 B1 | 6/2003 | Yamazaki et al. |
| 6,027,495 | A | 2/2000 | Miller | 6,602,245 B1 | 8/2003 | Thiberg |
| 6,030,399 | A | 2/2000 | Ignotz et al. | 6,605,080 B1 | 8/2003 | Altshuler et al. |
| 6,032,071 | A | 2/2000 | Binder | 6,629,971 B2 | 10/2003 | McDaniel |
| RE36,634 | E | 3/2000 | Ghaffari | 6,629,989 B2 | 10/2003 | Akita |
| 6,036,684 | A | 3/2000 | Tankovich et al. | 6,632,219 B1 | 10/2003 | Baranov et al. |
| 6,050,990 | A | 4/2000 | Tankovich et al. | 6,635,075 B2 | 10/2003 | Li et al. |
| D424,197 | S | 5/2000 | Sydlowski et al. | 6,641,600 B1 | 11/2003 | Kohler |
| 6,056,738 | A | 5/2000 | Marchitto et al. | 6,648,904 B2 | 11/2003 | Altshuler et al. |
| 6,059,820 | A | 5/2000 | Baronov | 6,653,618 B2 | 11/2003 | Zenzie |
| 6,074,382 | A | 6/2000 | Asah et al. | 6,660,000 B2 | 12/2003 | Neuberger et al. |
| 6,080,146 | A | 6/2000 | Altshuler et al. | 6,663,620 B2 | 12/2003 | Altshuler et al. |
| 6,086,580 | A | 7/2000 | Mordon et al. | 6,663,658 B1 | 12/2003 | Kollias et al. |
| 6,096,029 | A | 8/2000 | O'Donnell, Jr. | 6,663,659 B2 | 12/2003 | McDaniel |
| 6,096,209 | A | 8/2000 | O'Brien et al. | 6,676,654 B1 | 1/2004 | Balle-Petersen et al. |
| 6,104,959 | A | 8/2000 | Spertell | 6,679,837 B2 | 1/2004 | Daikuzono |
| 6,117,129 | A | 9/2000 | Mukai | 6,685,699 B1 | 2/2004 | Eppstein et al. |
| 6,120,497 | A | 9/2000 | Anderson et al. | 6,689,124 B1 | 2/2004 | Thiberg |
| 6,142,939 | A | 11/2000 | Eppstein et al. | 6,709,269 B1 | 3/2004 | Altshuler |
| 6,149,644 | A | 11/2000 | Xie | 6,709,446 B2 | 3/2004 | Lundahl et al. |
| 6,162,055 | A | 12/2000 | Montgomery et al. | 6,723,090 B2 | 4/2004 | Altshuler et al. |
| 6,162,211 | A | 12/2000 | Tankovich et al. | 6,743,222 B2 | 6/2004 | Durkin et al. |
| 6,162,212 | A | 12/2000 | Kreindel et al. | 6,770,069 B1 | 8/2004 | Hobart et al. |
| 6,173,202 | B1 | 1/2001 | Eppstein et al. | 6,790,205 B1 | 9/2004 | Yamazaki et al. |
| 6,174,325 | B1 | 1/2001 | Eckhouse | 6,808,532 B2 | 10/2004 | Andersen et al. |
| 6,176,854 | B1 | 1/2001 | Cone | RE38,670 E | 12/2004 | Asah et al. |
| 6,183,434 | B1 | 2/2001 | Eppstein | 6,878,144 B2 * | 4/2005 | Altshuler et al. ............... 606/9 |
| 6,183,500 | B1 | 2/2001 | Kohler | 6,888,319 B2 | 5/2005 | Inochkin et al. |
| 6,183,773 | B1 | 2/2001 | Anderson | 7,041,100 B2 * | 5/2006 | Kreindel ..................... 606/41 |
| 6,187,001 | B1 | 2/2001 | Azar et al. | 7,097,639 B1 * | 8/2006 | Almeida ........................ 606/9 |
| 6,197,020 | B1 | 3/2001 | O'Donnell | 7,198,634 B2 * | 4/2007 | Harth et al. ................... 607/90 |
| 6,210,425 | B1 | 4/2001 | Chen | 2001/0041886 A1 | 11/2001 | Durkin et al. |
| 6,214,034 | B1 | 4/2001 | Azar | 2002/0005475 A1 | 1/2002 | Zenzie |
| 6,228,075 | B1 | 5/2001 | Furumoto | 2002/0026225 A1 | 2/2002 | Segal |
| 6,229,831 | B1 | 5/2001 | Nightingale et al. | 2002/0091377 A1 | 7/2002 | Anderson et al. |
| 6,235,016 | B1 | 5/2001 | Stewart | 2002/0123745 A1 | 9/2002 | Svaasand et al. |
| 6,236,891 | B1 | 5/2001 | Ingel et al. | 2002/0128635 A1 | 9/2002 | Altshuler et al. |
| 6,245,093 | B1 | 6/2001 | Li et al. | 2002/0128695 A1 * | 9/2002 | Harth et al. ................... 607/88 |
| 6,263,233 | B1 | 7/2001 | Zavislan et al. | 2002/0161357 A1 | 10/2002 | Anderson et al. |
| 6,264,649 | B1 | 7/2001 | Whitcroft et al. | 2002/0173780 A1 * | 11/2002 | Altshuler et al. ............... 606/9 |
| 6,267,780 | B1 | 7/2001 | Streeter | 2003/0004499 A1 | 1/2003 | McDaniel |
| 6,273,884 | B1 | 8/2001 | Altshuler et al. | 2003/0023283 A1 | 1/2003 | McDaniel |
| 6,273,885 | B1 | 8/2001 | Koop et al. | 2003/0032900 A1 | 2/2003 | Ella |
| 6,280,438 | B1 | 8/2001 | Eckhouse et al. | 2003/0032950 A1 | 2/2003 | Altshuler et al. |
| 6,283,956 | B1 | 9/2001 | McDaniel | 2003/0036680 A1 | 2/2003 | Black |
| 6,290,713 | B1 | 9/2001 | Russell | 2003/0055414 A1 | 3/2003 | Altshuler et al. |
| 6,306,130 | B1 | 10/2001 | Anderson et al. | 2003/0057875 A1 | 3/2003 | Inochkin et al. |
| 6,319,274 | B1 | 11/2001 | Shadduck | 2003/0065314 A1 | 4/2003 | Altshuler et al. |
| 6,340,495 | B1 | 1/2002 | Sumian et al. | 2003/0100936 A1 | 5/2003 | Altshuler et al. |
| 6,343,933 | B1 | 2/2002 | Montgomery et al. | 2003/0109787 A1 | 6/2003 | Black |
| 6,350,276 | B1 | 2/2002 | Knowlton | 2003/0109860 A1 | 6/2003 | Black |
| 6,354,370 | B1 | 3/2002 | Miller et al. | 2003/0129154 A1 | 7/2003 | McDaniel |
| 6,358,272 | B1 | 3/2002 | Wilden | 2003/0187486 A1 | 10/2003 | Savage et al. |
| 6,383,177 | B1 | 5/2002 | Balle-Petersen et al. | 2003/0195494 A1 | 10/2003 | Altshuler et al. |
| 6,387,089 | B1 | 5/2002 | Kreindel et al. | 2003/0199859 A1 | 10/2003 | Altshuler et al. |
| 6,402,739 | B1 | 6/2002 | Neev | 2003/0232303 A1 | 12/2003 | Black |
| 6,406,474 | B1 | 6/2002 | Neuberger et al. | 2004/0006332 A1 | 1/2004 | Black |
| 6,424,852 | B1 | 7/2002 | Zavislan | 2004/0010298 A1 | 1/2004 | Altshuler et al. |
| 6,425,912 | B1 | 7/2002 | Knowlton | 2004/0015156 A1 | 1/2004 | Vasily |
| 6,436,094 | B1 | 8/2002 | Reuter | 2004/0024388 A1 | 2/2004 | Altshuler |
| 6,461,296 | B1 | 10/2002 | Desai | 2004/0030326 A1 | 2/2004 | Altshuler et al. |
| 6,471,712 | B2 | 10/2002 | Burres | 2004/0034319 A1 | 2/2004 | Anderson et al. |
| 6,471,716 | B1 | 10/2002 | Pecukonis | 2004/0034341 A1 | 2/2004 | Altshuler et al. |
| 6,475,211 | B2 | 11/2002 | Chess et al. | 2004/0073079 A1 | 4/2004 | Altshuler et al. |
| 6,494,900 | B1 | 12/2002 | Salansky et al. | 2004/0082940 A1 | 4/2004 | Black et al. |
| 6,508,785 | B1 | 1/2003 | Eppstein | 2004/0085026 A1 | 5/2004 | Inochkin et al. |
| 6,508,813 | B1 | 1/2003 | Altshuler et al. | 2004/0093042 A1 | 5/2004 | Altshuler et al. |
| 6,511,475 | B1 | 1/2003 | Altshuler et al. | 2004/0133251 A1 | 7/2004 | Altshuler et al. |
| 6,514,243 | B1 | 2/2003 | Eckhouse et al. | 2004/0143920 A1 | 7/2004 | Nanda |

| | | | |
|---|---|---|---|
| 2004/0147984 A1 | 7/2004 | Altshuler et al. | |
| 2004/0162549 A1 | 8/2004 | Altshuler et al. | |
| 2004/0162596 A1 | 8/2004 | Altshuler et al. | |
| 2004/0191729 A1 | 9/2004 | Altshuler et al. | |
| 2004/0193235 A1 | 9/2004 | Altshuler et al. | |
| 2004/0193236 A1 | 9/2004 | Altshuler et al. | |
| 2004/0199227 A1 | 10/2004 | Altshuler et al. | |
| 2004/0204745 A1 | 10/2004 | Altshuler et al. | |
| 2004/0210276 A1 | 10/2004 | Altshuler et al. | |
| 2004/0214132 A1 | 10/2004 | Altshuler | |
| 2004/0225339 A1 | 11/2004 | Yaroslavsky et al. | |
| 2004/0230258 A1 | 11/2004 | Altshuler et al. | |
| 2005/0038418 A1 | 2/2005 | Altshuler et al. | |
| 2005/0049582 A1 | 3/2005 | DeBenedictis et al. | |
| 2005/0049658 A1 | 3/2005 | Connors et al. | |
| 2005/0107849 A1 | 5/2005 | Altshuler et al. | |

FOREIGN PATENT DOCUMENTS

| | | |
|---|---|---|
| AU | 1851583 | 3/1984 |
| DE | 3837248 A1 | 5/1990 |
| DE | 9102407 | 7/1991 |
| EP | 0142671 A1 | 5/1985 |
| EP | 0565331 A2 | 10/1993 |
| EP | 0598984 A1 | 6/1994 |
| EP | 0724894 A2 | 8/1996 |
| EP | 0726083 A2 | 8/1996 |
| EP | 0736308 A2 | 10/1996 |
| EP | 0743029 | 11/1996 |
| EP | 0755698 A2 | 1/1997 |
| EP | 0763371 A2 | 3/1997 |
| EP | 0765673 A2 | 4/1997 |
| EP | 0765674 A2 | 4/1997 |
| EP | 0783904 A2 | 7/1997 |
| EP | 0884066 | 12/1998 |
| EP | 0885629 | 12/1998 |
| EP | 1038505 A2 | 9/2000 |
| EP | 1138349 | 10/2001 |
| EP | 1147785 | 10/2001 |
| EP | 1219258 A1 | 3/2002 |
| EP | 1226787 | 7/2002 |
| EP | 1 457 234 A2 | 9/2004 |
| FR | 2199453 | 4/1974 |
| FR | 2591902 A1 | 6/1987 |
| GB | 1546625 | 5/1979 |
| GB | 2044908 A | 10/1980 |
| GB | 2123287 A | 2/1984 |
| GB | 2356570 | 5/2001 |
| GB | 2360946 A | 10/2001 |
| GB | 2368020 | 4/2002 |
| GB | 2390021 | 12/2003 |
| GB | 2397528 | 7/2004 |
| JP | 2001145520 | 5/2001 |
| JP | 2003192809 | 2/2005 |
| RU | 2082337 C1 | 6/1997 |
| RU | 2089126 C1 | 10/1997 |
| RU | 2089127 C1 | 10/1997 |
| RU | 2096051 C1 | 11/1997 |
| RU | 2122848 C1 | 10/1998 |
| WO | WO 86/02783 A1 | 5/1986 |
| WO | WO 88/04592 | 6/1988 |
| WO | WO 90/00420 A1 | 1/1990 |
| WO | WO 91/13652 A1 | 9/1991 |
| WO | WO 92/16338 A1 | 10/1992 |
| WO | WO 92/19165 A1 | 11/1992 |
| WO | WO 93/05920 A1 | 4/1993 |
| WO | WO 95/15725 A1 | 6/1995 |
| WO | WO 95/32441 A1 | 11/1995 |
| WO | WO 96/23447 A1 | 8/1996 |
| WO | WO 96/25979 A1 | 8/1996 |
| WO | WO 96/36396 | 11/1996 |
| WO | WO 96/41579 | 12/1996 |
| WO | WO 97/13458 A1 | 4/1997 |
| WO | WO 98/04317 A1 | 2/1998 |
| WO | WO 98/24507 A1 | 6/1998 |
| WO | WO 98/51235 A1 | 11/1998 |
| WO | WO 98/52481 A1 | 11/1998 |
| WO | WO 98/58595 | 12/1998 |
| WO | WO 99/17666 | 4/1999 |
| WO | WO 99/17667 | 4/1999 |
| WO | WO 99/27997 A1 | 6/1999 |
| WO | WO 99/29243 A1 | 6/1999 |
| WO | WO 99/38569 A1 | 8/1999 |
| WO | WO 99/46005 A1 | 9/1999 |
| WO | WO 99/49937 A1 | 10/1999 |
| WO | WO 00/02491 | 1/2000 |
| WO | WO 00/03257 A1 | 1/2000 |
| WO | WO 00/32272 | 6/2000 |
| WO | WO 00/40266 | 7/2000 |
| WO | WO 00/43070 | 7/2000 |
| WO | WO 00/44294 A1 | 8/2000 |
| WO | WO 00/64537 | 11/2000 |
| WO | WO 00/71045 A1 | 11/2000 |
| WO | WO 00/74583 | 12/2000 |
| WO | WO 00/74781 A1 | 12/2000 |
| WO | WO 00/78242 A1 | 12/2000 |
| WO | WO 01/03257 A1 | 1/2001 |
| WO | WO 01/26573 | 4/2001 |
| WO | WO 01/34048 A1 | 5/2001 |
| WO | WO 01/42671 A1 | 6/2001 |
| WO | WO 01/54606 A1 | 8/2001 |
| WO | WO 01/54770 | 8/2001 |
| WO | WO 01/78830 A2 | 10/2001 |
| WO | WO 02/053050 A1 | 7/2002 |
| WO | WO 02/069825 A2 | 9/2002 |
| WO | WO 02/094116 A1 | 11/2002 |
| WO | WO 2004/073537 | 9/2004 |
| WO | WO 2004/084752 | 10/2004 |
| WO | WO 2004/086947 A2 | 10/2004 |
| WO | WO 2005/007003 A1 | 1/2005 |

OTHER PUBLICATIONS

Altshuler et al., "Extended theory of selective photothermolysis," Lasers in Surgery and Medicine, vol. 29, pp. 416-432, 2001.

Amy et al., "Selective mitochondrial damage by a ruby laser microbeam: An electron microscopic study," Science, vol. 15, pp. 756-758, Nov. 1965.

Anderson et al., "The optics of human skin," Journal of Investigative Dermatology, vol. 77, No. 1, pp. 13-19, 1981.

Anderson et al., "Selective photothermolysis: Precise microsurgery by selective absorption of pulsed radiation," Science, vol. 220, pp. 524-527, Apr. 1983.

Belikov et al., "Identification of enamel and dentine under tooth laser treatment," SPIE vol. 2623, Progress in Biomedical Optics Europe Series, Proceedings of Medical Applications of Lasers III, pp. 109-116, Sep. 1995.

Dover et al., "Pigmented guinea pig skin irradiated with Q-switched ruby laser pulses," Arch Dermatol, vol. 125, pp. 43-49, Jan. 1989.

Finkelstein et al., "Epilation of hair-bearing urethral grafts using the neodymium:yag surgical laser," Journal of Urology, vol. 146, pp. 840-842, Sep. 1991.

L. Goldman, Biomedical Aspects of the Laser, Springer-Verlag New York Inc., publishers, Chapts. 1, 2, & 23, 1967.

L. Goldman, "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

L. Goldman, "Effects of new laser systems on the skin," Arch Dermatol., vol. 108, pp. 385-390, Sep. 1973.

L. Goldman, "Laser surgery for skin cancer," New York State Journal of Medicine, pp. 1897-1900, Oct. 1977.

L. Goldman, "Surgery by laser for malignant melanoma," J. Dermatol. Surg. Oncol., vol. 5, No. 2, pp. 141-144, Feb. 1979.

L. Goldman, "The skin," Arch Environ Health, vol. 18, pp. 434-436, Mar. 1969.

L. Goldman & D.F. Richfield, "The effect of repeated exposures to laser beams," Acta derm.-vernereol., vol. 44, pp. 264-268, 1964.

L. Goldman & R.J. Rockwell, "Laser action at the cellular level," JAMA, vol. 198, No. 6, pp. 641-644, Nov. 1966.

L. Goldman & R.G. Wilson, "Treatment of basal cell epithelioma by laser radiation," JAMA, vol. 189, No. 10, pp. 773-775.

L. Goldman et al., The biomedical aspects of lasers, JAMA, vol. 188, No. 3, pp. 302-306, Apr. 1964.

L. Goldman et al., "Effect of the laser beam on the skin, Preliminary report" Journal of Investigative Dermatology, vol. 40, pp. 121-122, 1963.

L. Goldman et al., "Effect of the laser beam on the skin, III. Exposure of cytological preparations," Journal of Investigative Dermatology, vol. 42, pp. 247-251, 1964.

L. Goldman et al., "Impact of the laser on nevi and melanomas," Archives of Dermatology, vol. 90, pp. 71-75, Jul. 1964.

L. Goldman et al., "Laser treatment of tattoos, A preliminary survey of three year's clinical experience," JAMA, vol. 201, No. 11, pp. 841-844, Sep. 1967.

L. Goldman et al., "Long-term laser exposure of a senile freckle," ArchEnviron Health, vol. 22, pp. 401-403, Mar. 1971.

L. Goldman et al., "Pathology, Pathology of the effect of the laser beam on the skin," Nature, vol. 197, No. 4870, pp. 912-914, Mar. 1963.

L. Goldman et al., "Preliminary investigation of fat embolization from pulsed ruby laser impacts of bone," Nature, vol. 221, pp. 361-363, Jan. 1969.

L. Goldman et al., "Radiation from a Q-switched ruby laser, Effect of repeated impacts of power output of 10 megawatts on a tattoo of man," Journal of Investigative Dermatology, vol. 44, pp. 69-71, 1965.

L. Goldman et al., "Replica microscopy and scanning electron microscopy of laser impacts on the skin," Journal of Investigative Dermatology, vol. 52, No. 1, pp. 18-24, 1969.

Grossman et al., "Damage to hair follicles by normal-mode ruby laser pulses," Journal of he American Academy of Dermatology, vol. 35, No. 6, pp. 889-894, Dec. 1996.

Klein et al., "Biological effects of laser radiation 1.,"Northeast Electroncis Research and Engineering Meeting, NEREM Record, IEEE catalogue No. F-60, pp. 108-109, 1965.

Kuhns et al., "Laser injury in skin," Laboratory Investigation, vol. 17, No. 1, pp. 1-13, Jul. 1967.

Kuhns et al., "Biological effects of laser radiation II Effects of laser irradiation on the skin," NEREM Record, pp. 152-153, 1965.

Margolis et al., "Visible action spectrum for melanin-specific selective photothermolysis," Lasers in Surgery and Medicine, vol. 9, pp. 389-397, 1989.

J.A. Parrish, "Selective thermal effects with pulsed irradiation from lasers: From organ to organelle," Journal of Investigative Dermatology, vol. 80, No. 6 Supplement, pp. 75s-80s, 1983.

Polla et al., "Melanosomes are a primary target of Q-switched ruby laser irradiation in guinea pig skin," Journal of Investigative Dermatology, vol. 89, No. 3, pp. 281-286, Sep. 1987.

Riggle et al., "Laser effects on normal and tumor tissue," Laser Applications in Medicine and Biology, vol. 1, M.L. Wolbarsht, editor, Plenum Press, publishers, Chapter 3, pp. 35-65, 1971.

Shimbashi et al., "Ruby laser treatment of pigmented skin lesions," Aesth. Plast. Surg., vol. 19, pp. 225-229, 1995.

Stratton et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

Taylor et al., "Treatment of tattoos by Q-switched ruby laser," Arch. Dermatol. vol. 126, pp. 893-899, Jul. 1990.

V.V. Tuchin, "Laser light scattering in biomedical diagnostics and therapy," Journal of Laser Applications, vol. 5, No. 2-3, pp. 43-60, 1993.

Watanabe et al, "Comparative studies of femtosecond to microsecond laser pulses on selective pigmented cell injury in skin," Photochemistry and Photobiology, vol. 53, No. 6, pp. 757-762, 1991.

Welch et al., "Evaluation of cooling techniques for the protection of the pidermis during HD-yag laser irradiation of the skin," Neodymium-Yag Laser in Medicine and Surgery, Elsevier Science Publishing Co., publisher, pp. 195-204, 1983.

Yules et al., "The effect of Q-switched ruby laser radiation on dermal tattoo pigment in man," Arch Surg, vol. 95, pp. 179-180, Aug. 1967.

Zeitler et al., "Laser Characteristics that Might be Useful in Biology," *Laser Applications in Medicine and Biology*, 1:1-16, 1971.

Abstracts Nos. 17-19, Lasers in Surgery and Medicine, ASLMS, Supplement 13, 2001.

Abstracts Nos. 219-223, ASLMS.

Abstracts, various.

Invention description to certificate of authorship, No. 532304, "The way of investigation of radiation time structure of optical quantum generator".

Invention description to certificate of authorship, No. 719439, "The ring resonator of optical quantum generator".

Invention description to certificate of authorship, No. 741747, "the modulator of optical radiation intensity".

Invention description to certificate of authorship, No. SU 1257475 A1, "Laser interferometric device to determine no-linearity of an index of refraction of optical medium".

Invention description to certificate of authorship, No. SU 1326962 A1, "The way of determination of non-linearity of an index of refraction of optical medium".

Altea Therapeutics—Medicines Made Better (single page website print-out).

P. Bjerring et al., "Selective Non-Ablative Wrinkle Reduction by Laser," J Cutan Laser Ther, vol. 2, pp. 9-15, 2000.

Derma Chiller advertisement (2 pages) from Paradigm Trex.

Doukas et al., "Transdermal Drug Delivery With a Pressure Wave," Advanced Drug Delivery Reviews 56 (2004), pp. 559-579.

Ohshiro et al., "The Ruby and Argon Lasers in the Treatment of the Naevi," Annals Academy of Medicine, Apr. 1983, vol. 12, No. 2, pp. 388-395.

Sumian, C.C. et al., "A Preliminary Clinical And Histopathological Study Of Laser Skin Resurfacing Using A Frequency-Doubled Nd:YAG Laser After Application of Chromofilm®," Journal of Cutaneous Laser Therapy, vol. 1, pp. 159-166, 1999.

Sumian, C.C. et al., "Laser Skin Resurfacing Using A Frequency Doubled Nd:YAG Laser After Topical Application Of An Exogenous Chromophore," Lasers in Surgery and Medicine, vol. 25, pp. 43-50, 1999.

* cited by examiner

US 7,540,869 B2

METHOD AND APPARATUS FOR IMPROVED VASCULAR RELATED TREATMENT

RELATED APPLICATIONS

This non-provisional application claims the benefit under Title 35, U.S.C. § 119(e) of co-pending U.S. provisional application serial No. 60/343,811, filed Dec. 27, 2001, which is incorporated herein by reference.

FIELD OF THE INVENTION

This invention relates to methods and apparatus for improved vascular related treatments, and more particularly to methods and apparatus for treating vascular lesions, for skin rejuvenation and for other dermatological treatments where safety and efficacy are enhanced by using only selected portions of the optical spectrum.

BACKGROUND OF THE INVENTION

Optical radiation is currently used to treat a variety of dermatological conditions, including various vascular lesions (for example spider veins, facial telangiectasia, port wine stains, rosacea and erythema, spider angioma, poikloderma of civatte, pyogenic granuloma, venous lakes, cherry angioma, leg telangiectasia, varicose veins, and hemangioma), skin rejuvenation by regeneration of collagen in the affected area to improve skin texture, eliminating wrinkles, scars and the like, psoriasis, hair growth control, acne, etc. Conventional treatments for vascular lesions have involved the use of lasers operating in a wavelength band from approximately 520 nm to 600 nm for shallow veins, wavelengths at which blood has relatively high absorption and at wavelengths from approximately 750 nm to 1060 nm for deep veins, but have generally not operated at wavelengths below 488 nm. Where broad spectrum lamps are used, the lamps have typically been band-pass filtered to operate in a range of approximately 510 nm to 1,200 nm, depending on a number of factors, including the size of the vessel on which treatment is to be performed. For example, U.S. Pat. Nos. 5,620,478 and 5,755,751 reflect conventional wisdom, suggesting wavelength bands as follows:

Arteries less than 0.1 mm in diameter—520 to 650 nm;
Veins less than 0.1 mm in diameter—520 to 700 nm;
Vessels between 0.1-1.0 mm in diameter—550 to 1,000 nm; and
Larger vessels—600 to 1,000 nm.

However, most of the wavelength bands at which blood has conventionally been treated are also absorbed fairly strongly by melanin. Since there are melanin concentrations in the epidermis of substantially all individuals, such melanin typically being concentrated at the dermal/epidermal junction (DE junction) and there is significant melanin concentration in the epidermis for dark skinned or tanned individuals, the use of these wavelengths to treat vascular lesions and other dermatological and cosmetic conditions can also result in significant heating of the epidermis, and thus cause potential damage to the epidermis, especially for dark skinned patients. This has limited the optical radiation dosage which can be applied in some applications and has frequently required cooling of the epidermis, sometimes aggressive cooling, which can add significantly to the cost of the apparatus used for the treatment, and can also make the apparatus bulky and more difficult to use. Even with cooling, heating of the epidermis may result in some patient discomfort, and may even prevent treatment from being performed on certain very dark skinned individuals.

Similarly, water is present in all cells and intercellular space of the body so that targeting water can also result in the heating of epidermal tissue and other tissue outside of the desired treatment area. Thus, care must again be exercised to assure that the treatment does not result in undesired epidermal or other tissue damage. Because of this, phototreatment of vascular targets can currently be performed only by an experienced physician or other highly trained person in a clinical setting using expensive apparatus.

A need therefore exists for improved methods and apparatus, and in particular, safer and/or more effective methods and apparatus, for treating various vascular related conditions including, but not limited to, treating vascular lesions, performing skin regeneration, and treating other skin conditions associated with organs or other body elements having blood supply systems, particularly ones involving treatment of small blood vessels relatively close to the skin surface, for example within approximately 0.5 mm of the skin surface. Such small vessels would include veins and arteries in the papillary dermis in general, including the plexus, and in particular, small blood vessels in the plexus and spider veins. However, the need for safer and/or more effective treatment methods and apparatus also exists for deeper and/or larger vessels. Such safer and more effective treatment may facilitate the performance of such treatments in spas, salons, the home and other non-clinical settings.

SUMMARY OF THE INVENTION

In accordance with the above, this invention provides methods and apparatus for the safe and more effective treatment of various dermatological, including medical and cosmetic, conditions by the heating of blood vessels.

In accordance with one aspect of the invention, shallow vessels, primarily plexus vessels and superficial vessels/veins are heated by applying optical radiation to the vessels from a suitable source which radiation includes substantial radiation in a blue wavelength band of approximately 380-450 nm. The optical radiation may be monochromatic radiation in a wavelength range of approximately 400-450 nm, and more preferably in a range of approximately 410-440 nm. For superficial vessels, radiation from the source may also include radiation in a green-yellow wavelength band of 510 to 595 nm. The radiation may also be non-monochromatic, broadband radiation which, for this aspect of the invention, is in a blue (B) wavelength band from 380 to 450 nm, a green-yellow (GY) wavelength band from 500 to 610 nm, and near infrared (NIR) wavelength band from 800 to 1120 nm, and possibly up to 2800 nm The radiation may also have a double band spectrum including approximately in the blue band and also including in a green-yellow band or green-yellow and near infrared bands or blue and near infrared bands. Broadband radiation may have a triple band spectrum which also includes radiation within a band in the blue, the green-yellow and the near infrared (NIR). For the plexus and the superficial vessels one may choose between the blue and the green bands. Alternatively, a double-band spectrum may be of use incorporating both the blue and green-yellow bands or a triple band spectrum can be used. The treatment may be enhanced by applying pressure and/or cooling to the patient's skin which, among other things, removes blood from blood vessels above blood vessels for which treatment is desired.

In accordance with another aspect of the invention, a broadband optical radiation source is provided, and mechanisms are provided for filtering radiation from the source to pass only wavelengths from the source providing a safety ratio which is approximately at least one and for applying filtered radiation from the source to the blood vessels involved in the treatment. Wavelengths filtered from the radiation may include wavelengths from approximately 610 to 800 nm and preferably wavelengths from approximately 610 nm to 900 nm. Radiation having wavelengths from approximately 450 to 500 nm should also be filtered. Pressure and/or cooling may also be employed for this aspect of the invention. Stated another way, radiation passed as a result of the filtering may include radiation in a blue wavelength band and a green-yellow wavelength band, radiation in an NIR wavelength band also being included for some embodiments, with radiation between the included wavelength bands being filtered out. Other alternatives are that the passed wavelength bands include a blue wavelength band and an NIR wavelength band, at least some of the radiation therebetween being filtered, or green-yellow and NIR wavelength bands, with radiation there between being filtered out.

The invention may also involve filtering the radiation from a broadband source so as to pass to the blood vessels involved in the treatment only selected wavelengths which are in at least two of the blue, green-yellow and NIR wavelength bands, at least some of the radiation in wavelengths between the passed wavelength bands being filtered out. For some embodiments, radiation from all three of the bands is passed.

For another aspect of the invention, radiation from a broadband source is filtered to pass to the veins involved in the treatment only selected wavelengths from the source, the wavelengths passed and the duration of applied radiation pulses being selected to provide substantially uniform heating of each vein. More particularly, radiation passed is radiation in a green-yellow wavelength band and radiation in an NIR wavelength band, radiation between the bands being filtered out, and the pulse duration is approximately 0.1 to 100 times the thermal relaxation time of the vein involved in the treatment.

The foregoing and other objects, features and advantages of the invention will be apparent from the following more particular description of preferred embodiments of the invention as illustrated by the accompanying drawings.

IN THE DRAWINGS

FIG. 1 is a diagrammatic view of a section of a patient's skin with an apparatus suitable for practicing the teachings of the invention, in accordance with one aspect thereof, positioned thereon;

FIG. 2. is a plot of absorption coefficient against wavelength for the main skin chromophores, namely 1—water, 2—melanin, 3—vein blood, and 4—arteria blood;

FIG. 3. is a plot of penetration depth of light into the skin against wavelength for Fitzpatrick's skin types I and V;

DETAILED DESCRIPTION

Figure 1:
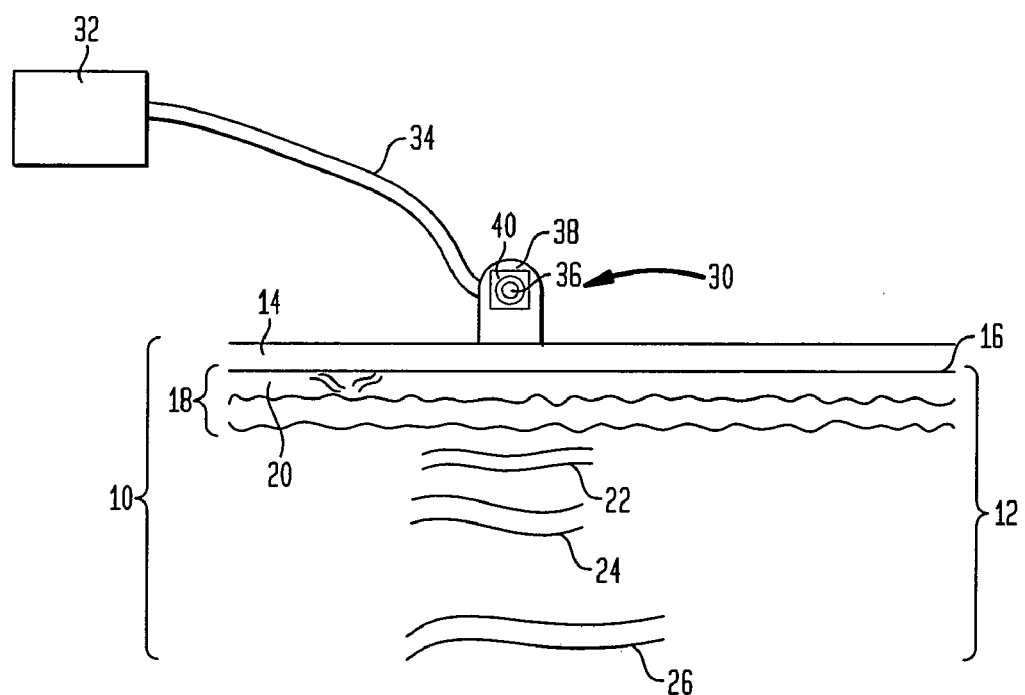

FIG. 1 is a graphic representation of a section of a person's skin 10 which includes a dermal layer 12 covered by an epidermal layer 14, which layers are separated by a dermal-epidermal (DE) junction or basal layer 16. The upper portion 18 of the dermis is referred to as the papillary dermis and extends roughly 300 microns into the skin, the upper portion of the papillary dermis, extending roughly 20-50 microns into the dermis, being referred to as the plexus 20. Plexus 20 (⅓ of epidermis thickness) is rich in very small blood vessels, most of which have diameters in the 5 to 20 micron range, with 10 microns being a typical diameter. These plexus vessels are typically at a depth of about 0.05-0.15 mm. Papillary dermis 18, including plexus 20, also contain the collagen and fibroblasts normally involved in skin restructuring for wrinkle removal, scar removal, treatment of skin indentations and treatment of other skin blemishes.

In addition to plexus vessels, the teachings of this invention may also be used in treatments involving the following vessels/veins:

Superficial veins 22, for example facial spider veins (typical depth 0.25-0.5 mm, typical diameter 0.05-0.3 mm);

Intermediate veins 24 (typical depth 0.5-1 mm, typical diameter 0.2-1 mm); and

Deep veins 26, for example leg veins, (typical depth 1-5 mm, typical diameter 1-several mm).

FIG. 1 also shows exemplary apparatus for practicing the teachings of the invention. This apparatus includes a head 30 which is preferably adapted to be in contact with the patients skin during treatment and a control box 32 connected to head 30 by an umbilical 34. A suitable light source of the type discussed later may be in head 30 or in box 32, umbilical 34 containing light guides in the latter case to deliver light from the source to the head, and containing electrical lines to operate the source in the former case. Box 32 would also normally include suitable controls for the apparatus and may also contain a cooling mechanism, the cooling medium in this case also passing to head 30 through umbilical 34.

While as indicated above, the light source may be any suitable light source and may be in either head 30 or control box 32, for purposes of illustration, the light source is shown in FIG. 1 as a lamp 36 in head 30 with a reflector 38 surrounding the lamp on three sides to direct light from the lamp to an output component 40 which may be a waveguide, lens, contact plate or other suitable output component. A tube 42 may also be provided surrounding lamp 36, which tube may perform a variety of functions known in the art.

Epidermis 14 in general, and DE junction 16 in particular, contain substantial quantities of melanin, the quantity of melanin at the DE junction increasing as the darkness of the patient's skin increases, being least for light, type I, skin and greatest for very dark, type VI, skin. As the skin becomes darker, there is also increasing amounts of melanin throughout the epidermis, although the largest concentration still remains at the DE junction. The DE junction is typically at about an 0.05-0.15 mm depth in the skin.

Figure 2:
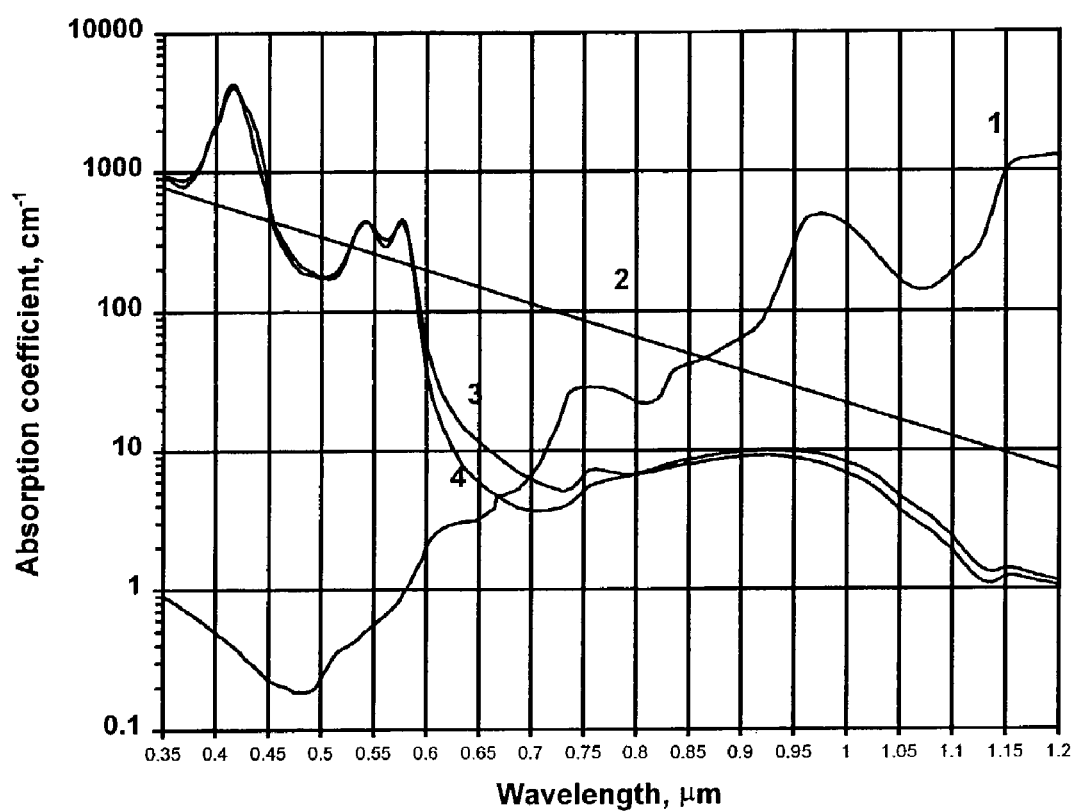

When dealing with the optical treatment of skin lesions, the absorption spectra of skin constituents are of primary interest. FIG. 2 shows the calculated absorption coefficients of water (×1000) (1), melanin (2), venous blood (3), and arterial blood (4) as a function of visible and near infrared wavelengths. For the calculations of FIG. 2, the hematocrit of both the arterial and venous blood is 0.4 and the value of oxygen saturation varies from 0.7 for venous blood to 0.9 for arterial blood. The concentration of melanin (eumelanin) is set to be the same as that in the basal layer/epidermis of type V skin.

Figure 3:
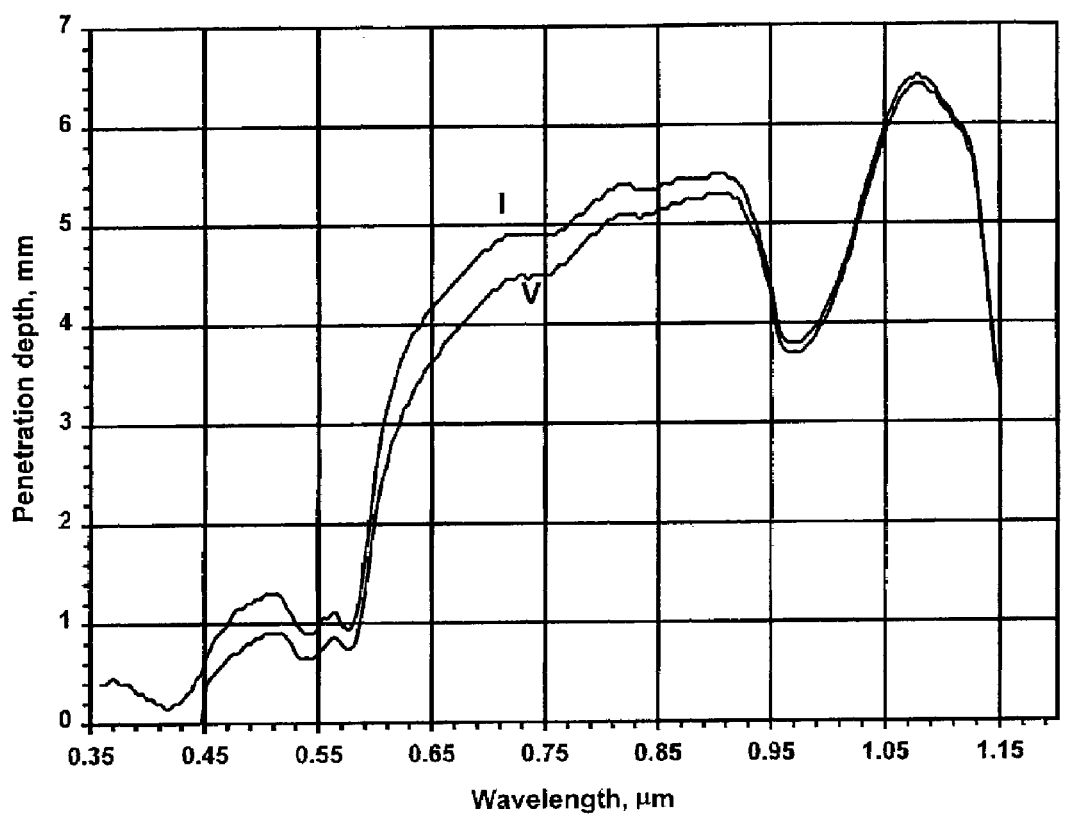

After entering the skin, collimated light loses its directivity and coherence (if present) and becomes diffuse at a distance of roughly 50 to 1000 micrometers due to multiple scattering on skin heterogeneities. To describe the thermal effect of the diffuse light, one typically uses a physical quantity known as radiance which is defined as the total light energy crossing the surface of a unit sphere for a unit time. The radiant exposure (fluence) is the integral of the radiance over the entire period of time that the light strikes the skin. When the diffuse light undergoes absorption, the resultant heat developed is proportional to the product of the radiance and the absorption coefficient. Backscattering in the skin causes the radiance at a point in the skin to exceed the input light flux to such point by up to several times. However, as depth in the skin increases, irradiance falls due to both scattering and absorption. The penetration depth of light into the skin may be defined for the following discussion as the depth at which the radiance becomes equal to the input flux. Using this definition, FIG. 3 shows the calculated penetration depth against wavelength for type I and V skin. As seen in this figure, penetration into the skin falls significantly for normal skin at wavelengths below 450 nm due to increased blood absorption. However, when an external force or cooling is applied to the upper skin surface to occlude the blood vessels comprising the upper vessel plexus, the penetration of light at wavelengths below 450 nm is significantly increased.

For purposes of this invention, a safety ratio S is defined such that $$S=\Delta T_v/\Delta T_b$$

where $\Delta T_v$ is the maximal temperature rise as a result of the treatment at the vessel being treated and $\Delta T_b$ is the maximal temperature rise as a result of heating at basal layer 16, such temperature rise being primarily due to melanin absorption. It is desired that this ratio be maximized in order to achieve efficient heating of the blood vessel while minimizing pain for the patient and other undesired side effects.

Another criterion of interest for the purpose of this invention is action efficiency (AE), which is the maximal temperature rise at the target (i.e. the blood vessel) per 1 J/cm² of the input light flux. The higher the AE value, the less energy is required from the radiation source and therefore, the lower both the device and treatment costs.

Figure 4A:
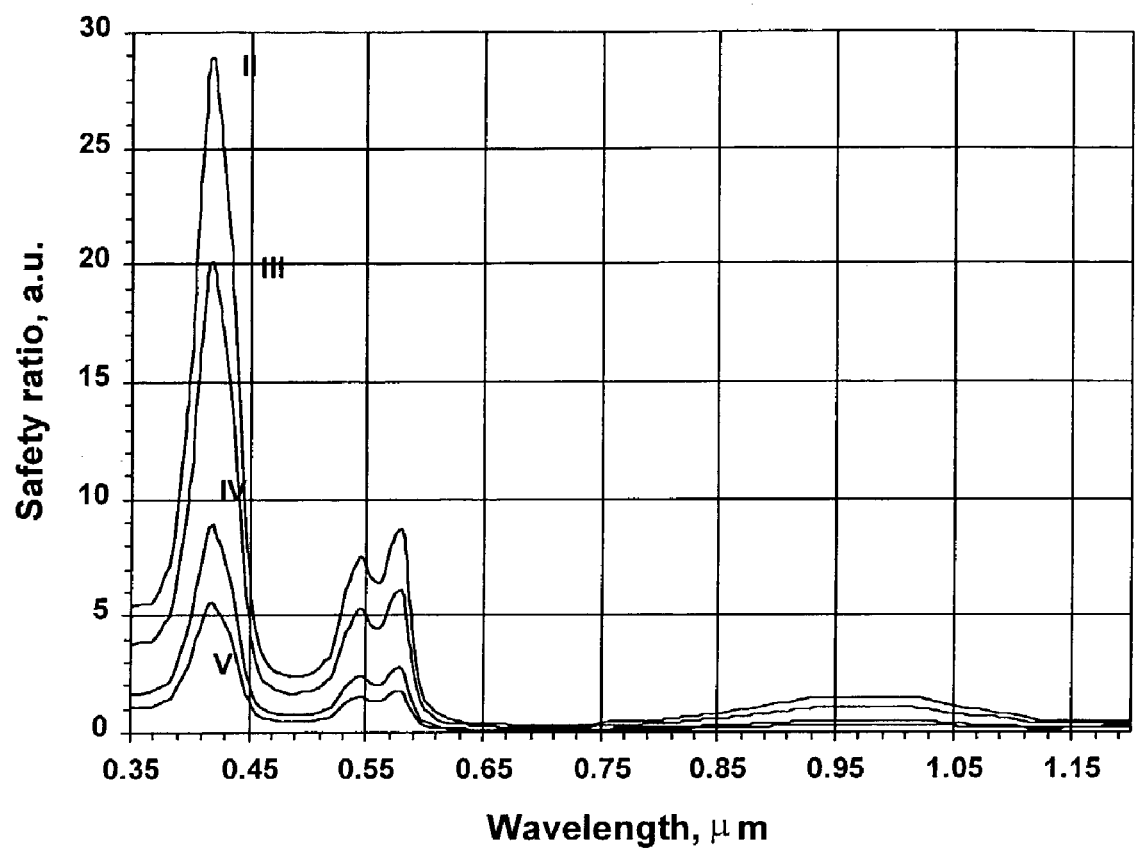
FIGS. 4a-4d are plots of safety ratio for plexus vessels, superficial veins, intermediate veins, and deep veins respectively using short light pulses.
Figure 4B:
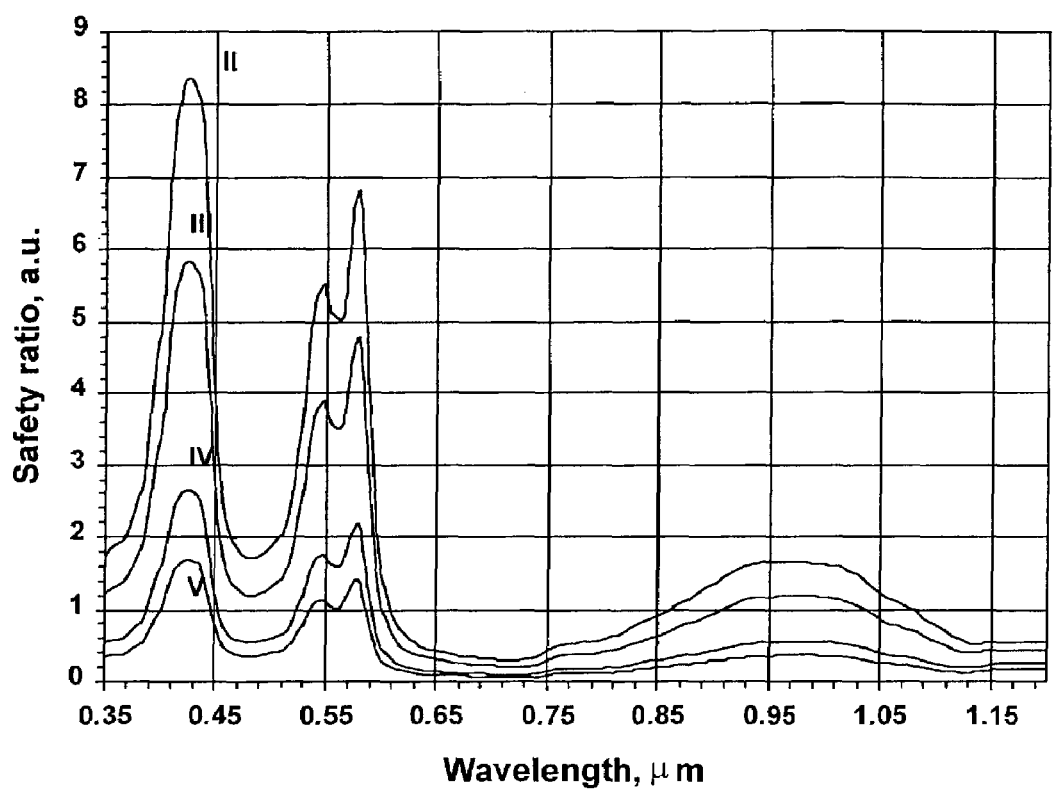
Figure 4C:
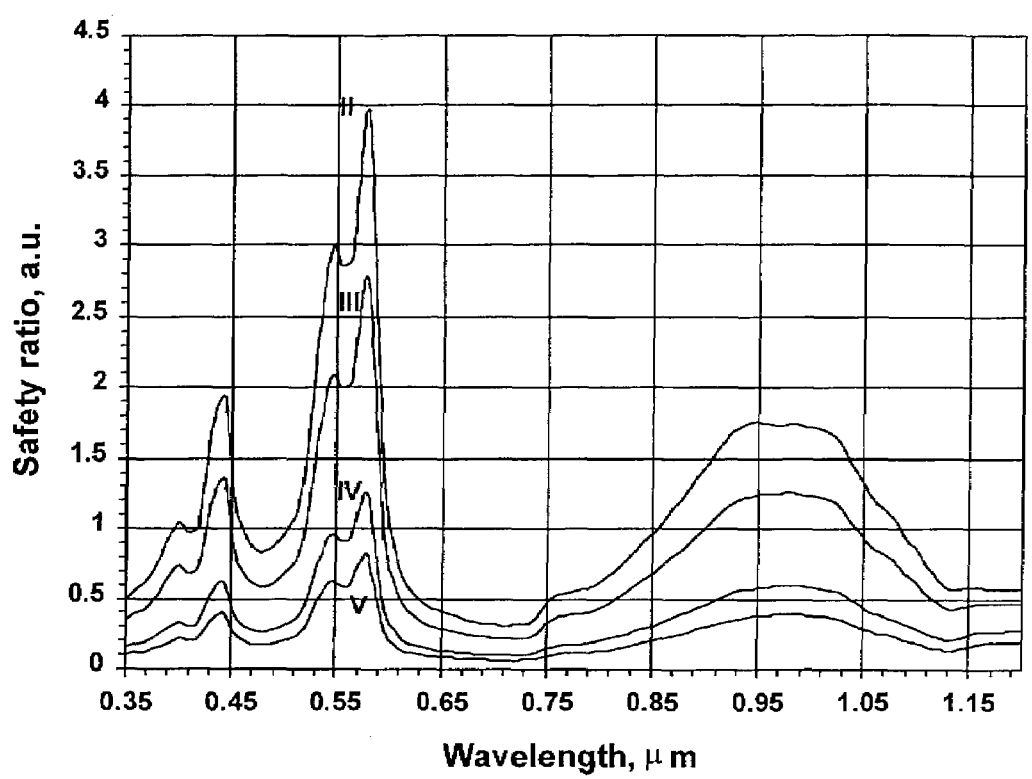
Figure 4D:
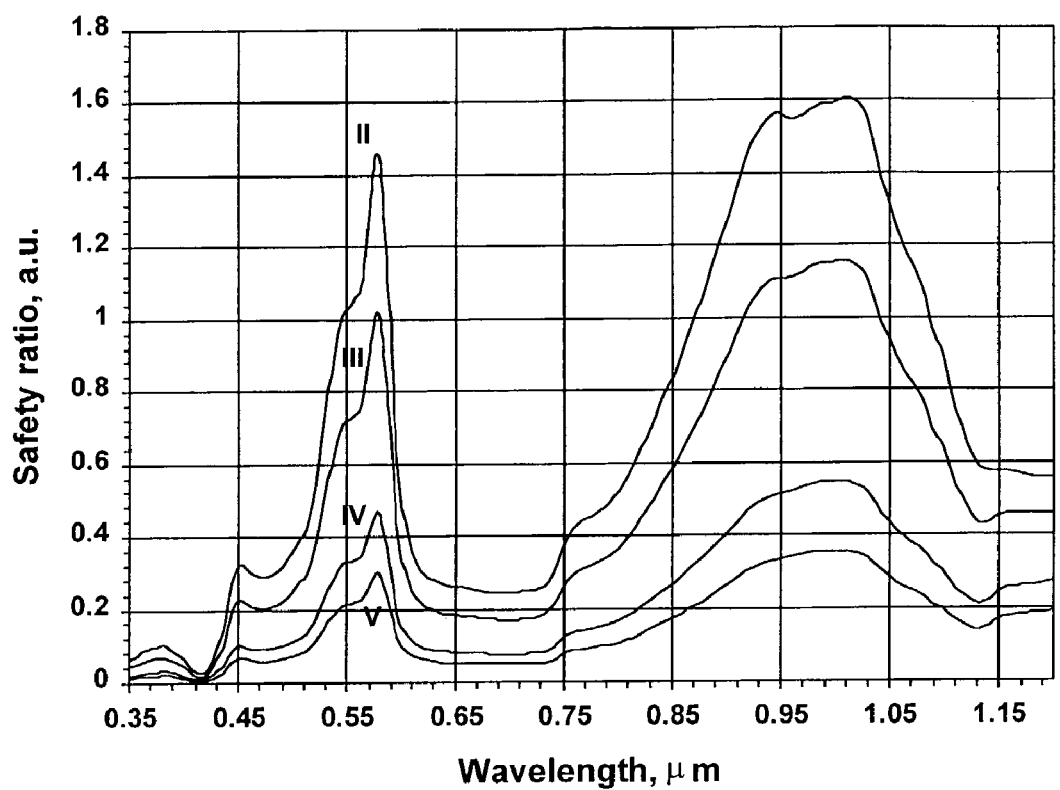
Figure 5A:
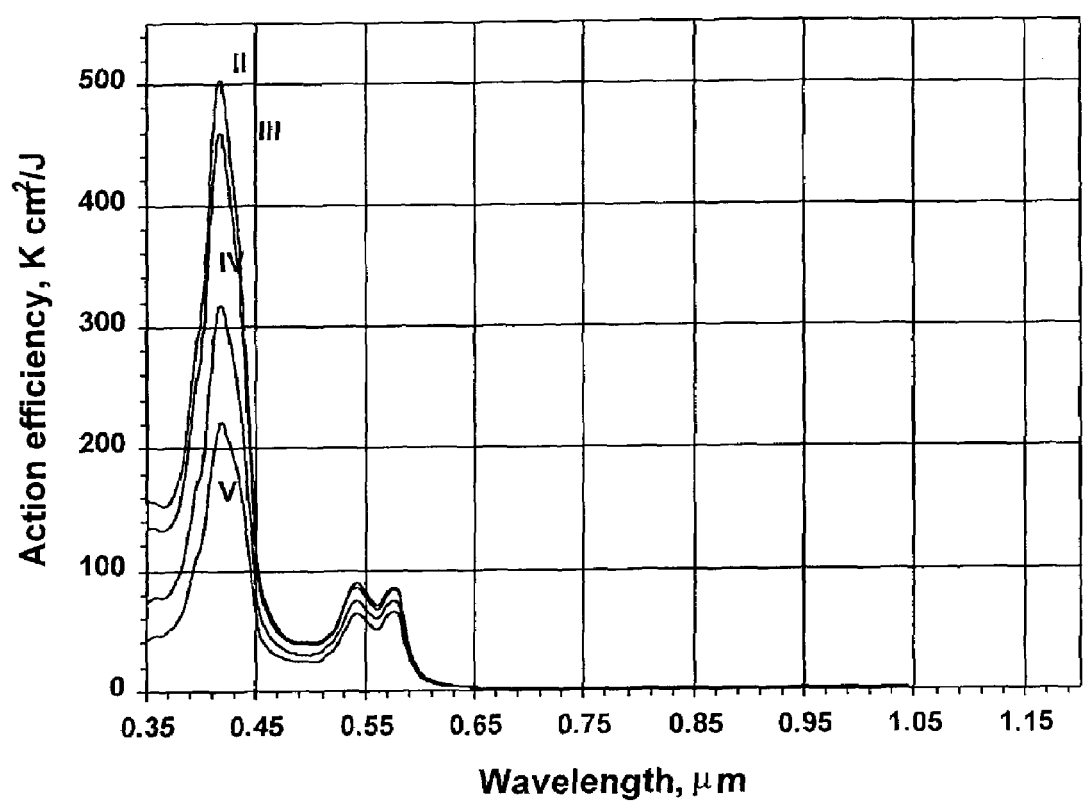
FIGS. 5a-5d are plots of action efficiency for plexus vessels, superficial veins, intermediate veins, and deep veins respectively using short light pulses.
Figure 5B:
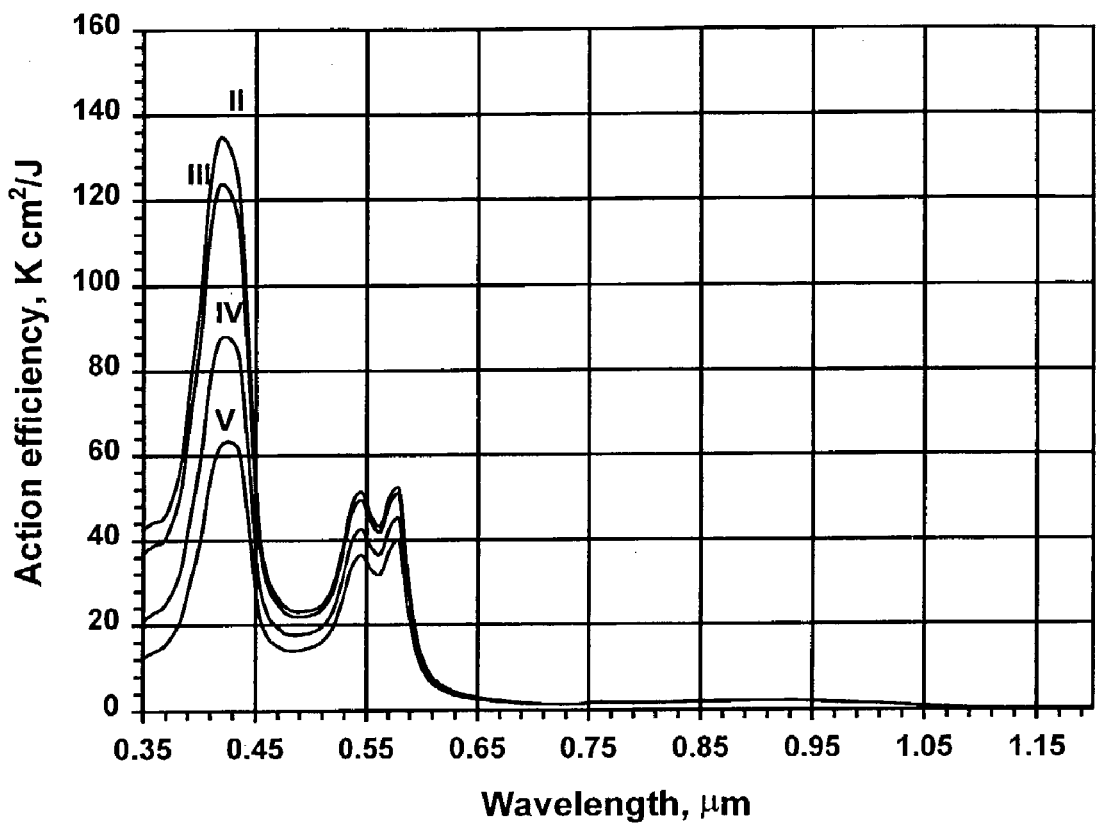
Figure 5C:
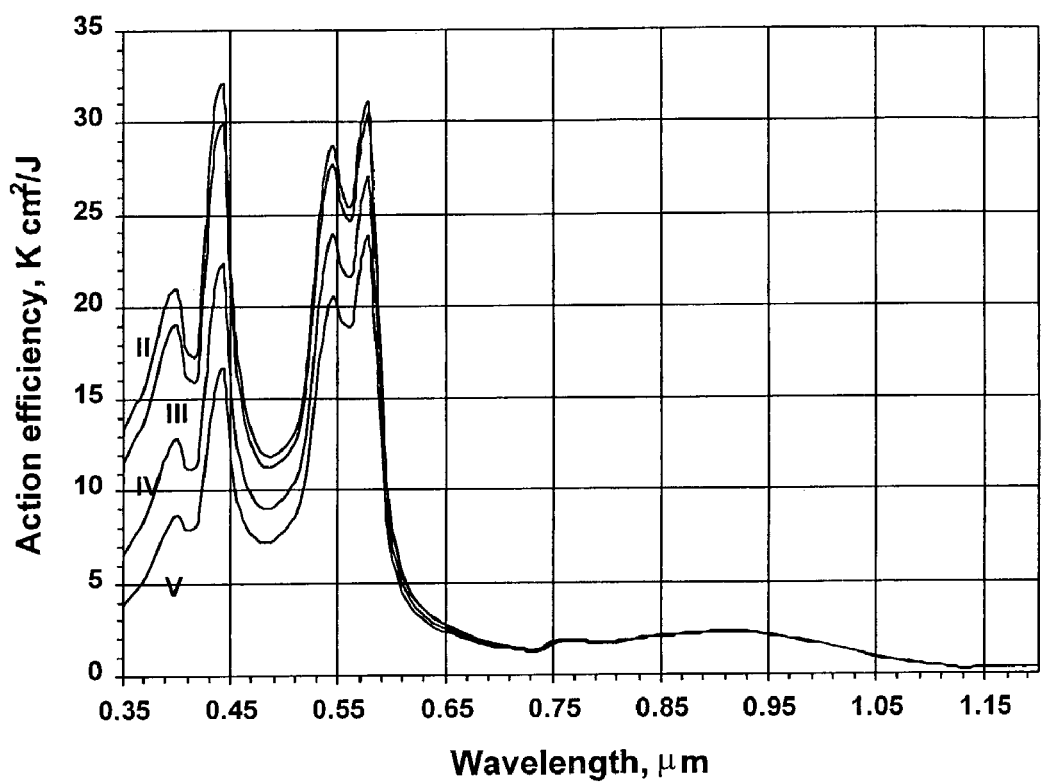
Figure 5D:
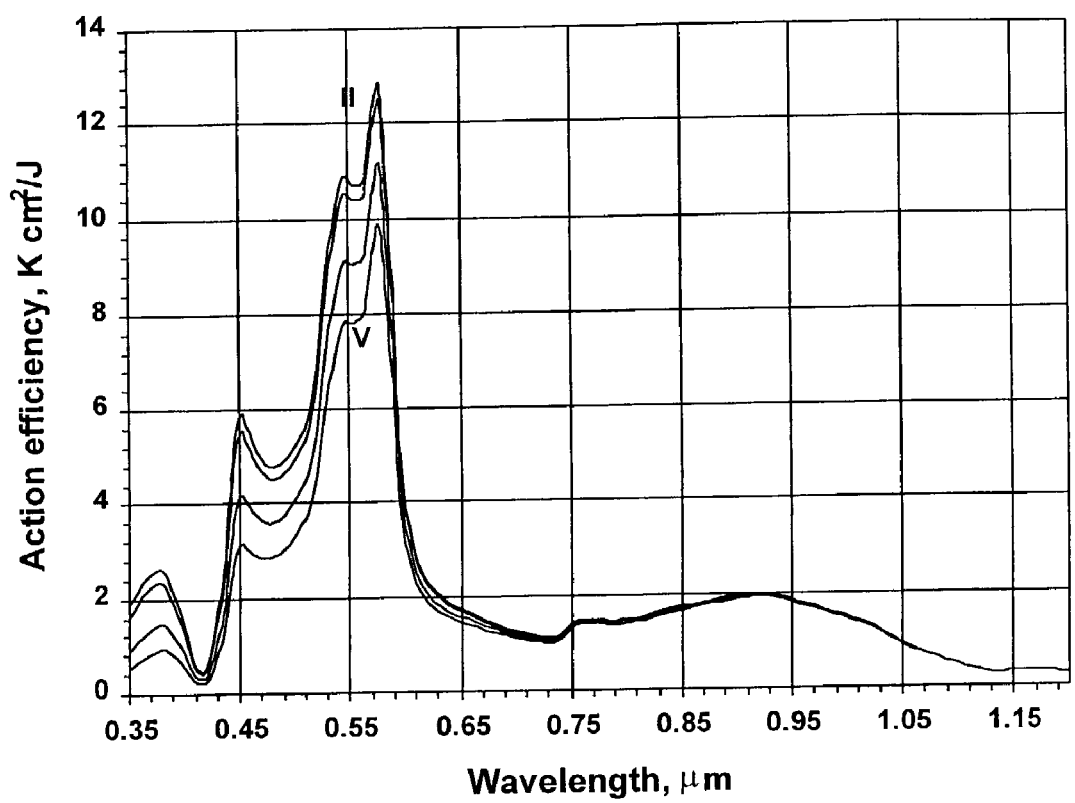

The specific results of computer simulations will now be considered for the following vessel types which differ in their diameter D and depth H:
  a. Plexus vessels (D=0.01 mm; H=0.1 mm). FIGS. 4a, 5a;
  b. Superficial vessels (D=0.2 mm; H=0.25 mm). FIGS. 4b, 5b;
  c. Intermediate vessels (D=H=0.5 mm). FIGS. 4c, 5c;
  d. Deep vessels (D=H=1 mm). FIGS. 4d, 5d.

The calculated S and AE for these vessel types for an infinitesimal pulse width shorter than the thermal relaxation time of the vessels are shown in FIGS. 4a-d and 5a-d, respectively. The Roman numerals from II to V on the plots indicate the Fitzpatrick's skin types. The safety ratio can be increased by using precooling, parallel cooling and/or longer pulsewidth.

It appears from the simulation data that the spectral regions most promising from the point of view of effective and safe vein/vessel treatment include:
  1. Blue range (B) 0.38-0.45 μm (380-450 nm);
  2. Green-yellow range (GY) 0.5-0.61 μm (500-610 nm);
  3. Near IR range (NIR) 0.8-1.12 μm (800-1120 nm).

Apparently, regions 1-3 are related to the aforementioned absorption bands of hemoglobin. The boarders of the B, G and NIR bands can be adjusted around the numbers shown above depending on the depth of the vessels and the patient's skin type. For example, for dark skin, the NIR band is preferably 0.9-1.12 μm, and the G range is preferably 0.53-0.61. For treatment of the plexus and/or superficial vessels, the NIR band can be extended, perhaps up to 2800 nm, to provide non selective heating of superficial parts of the skin. While this increases the action efficiency of the light and provides better use of energy from a broad band light source, it decreases the safety ratio of treatment This expanded NIR band should therefore be used carefully.

It should be understood that in any practical implementation of the invention, ideal filtration of a broad-band light source cannot be achieved. As a result, a certain percentage of light energy will be present at wavelengths outside the above-specified bands. Further, light energy may not be distributed absolutely uniformly within the bands due to natural limitations of the light sources and filtration techniques. These circumstances should not be considered as limiting the scope of the present invention.

Based on FIGS. 4 and 5, the B range (the Soret absorption band) provides clear advantages over the other two bands for plexus vessels only. For superficial veins, both the B and GY ranges give almost the same safety; however, the B range is somewhat better in respect to treatment efficiency. In the case of intermediate veins, the best safety is encountered for the GY range. Finally, for deep veins, maximum safety is attained using NIR light, however, the GY range provides better efficiency.

With these criteria in mind, it can be seen that the safety ratio has a maximum at approximately 0.42-0.44 μm (i.e. 420-440 nm), has a minimum at about 0.48 μm and then increases, having maximums at approximately 0.54 and 0.58 μm before falling off sharply at about 0.6 μm. The safety ratio rises again, getting close to 1 or over 1 for most skin types, particularly lighter skin types, at 0.8-1.12 μm (i.e. 800-1120 nm). The preferred wavelengths of treatment are dictated by the safety ratio, and in particular by selecting a wavelength or wavelength band which optimizes the safety ratio for coherent light and which primarily utilizes wavelengths having a safety ratio greater than 1 for incoherent light.

Therefore, for safe and effective treatment of vascular targets at depths up to 0.3 mm, monochromatic light sources with wavelengths within the B range can be used. Fluences needed for these treatments can be 2-6 times lower than with traditional treatment using KTP (532 nm) or dye ( 577-595 nm) lasers. The fluence for vascular treatments can be in the range 1-10 J/cm² for pulses shorter than or comparable with the thermal relaxation time (TRT) of the vessels (25 μs-25 ms). A twofold lower fluence can be used for skin texture or wrinkle improvement by plexus heating: 0.5-5 J/cm². However, because blue light does not penetrate much below the skin surface, it is best for plexus vessels and superficial veins and is of little value for intermediate veins. As discussed later, pressure to the skin over the vein to be treated and cooling of the skin can enhance treatment in general, and blue light treatment in particular, for superficial and intermediate veins.

There are some additional issues with the use of blue light in treating blood vessels. Optimum vessel closure can be achieved by denaturization of the endothelium that is in direct contact with blood. The penetration depth of blue light into blood is rather small, being at most 5-30 micrometers. As a result, the vessels undergo inhomogeneous heating. Therefore, the upper and lateral parts of the vein endothelium may be damaged with its lower part remaining intact. This may reduce the efficacy of vein treatment and can be cause of purpura. To solve this problem of inhomogeneous heating, two alternative approaches may be used:
1. The lasing wavelength may be offset from the absorption peaks of hemoglobin;
2. The pulsewidth may be extended.

From the above, it seems that choosing the appropriate regions of the spectrum and/or long pulswidths provide rather uniform vein heating. The minimal time needed to heat a vein uniformly to its damage temperature is called the thermal damage time (TDT). TDT is the time require to propagate a front of thermal damage to a certain depth in a vessel wall. Theoretical considerations show that the TDT may be from 1.5 to 100 times larger than the thermal relaxation time of the vessel. However, in some cases, the TDT may not exist (the temperature distribution in the vein may be very heterogeneous even in the steady state). Thus, using pulsewidths significantly (1.5-100 times) longer than the thermal relaxation time of the vessel being used in the treatment can permit more uniform heating to be achieved. However, this mode of treatment requires higher fluences, in the range of for example 10-200 $J/cm^2$, to be used.

Various types of monochromatic light sources can be used for vascular related treatments, including skin rejuvenation, using blue light, these lasers including semiconductor lasers, light emitting diode, GaAs semiconductor laser (790-900 nm) with second harmonic generator, OPO, fiber lasers with non linear converter, dye lasers, solid state lasers, etc.

According to FIGS. 4 and 5, lasers for vascular treatments should emit light in one of three bands:
Plexus vessels: B and/or GY;
Superficial vessels: GY and/or B and/or NIR;
Intermediate vessels: GY and/or NIR;
Deep vessels: GY and/or NIR.

More precise ranges of monochromatic (laser) wavelengths for vascular treatment are shown in Table 1.

By changing color temperature from 8000° K. to 3000° K., it is possible to shift the maximum of lamp energy from the blue light range (B) to near infrared range (NIR). For vascular treatment, infrared light with wavelength longer than 1100-1200 nm provides unselective skin heating and can cause pain and other undesirable side effects. The most dangerous wavelength ranges are around the peaks of water absorption at 1.45 μm and 1.94 μm (FIG. 2). The best way to eliminate these wavelengths is to use a water filter. In an example demonstrated by FIG. 6, the light passes through a 3 mm thick water filter prior to entering the skin. The water filter removes all spectral features at wavelengths corresponding to the water absorption bands. In order to eliminate potentially hazardous UV radiation from the output spectrum, absorptive glass filters (or other types of filters—e.g., dichroic) can be used. Filtration of short wave lengths is important for wavelengths shorter than 360 nm and is imperative for wavelengths shorter than 290 nm. Ce-doped quartz can be used as a material for such filtration.

For optimal treatment of vascular targets, the present invention suggests a new type of additional filtration, this additional filtration following from the fundamental curves in FIGS. 4-5. Optimal filtration for a therapeutic broad band light sources should meet the following criteria:
1. Maximal transmission of wavelengths with a safety ratio S>1;
2. Maximum attenuation of unwanted wavelengths with safety ratio S<1;
3. Maximally steep boundaries between the two regions.

Figure 7:
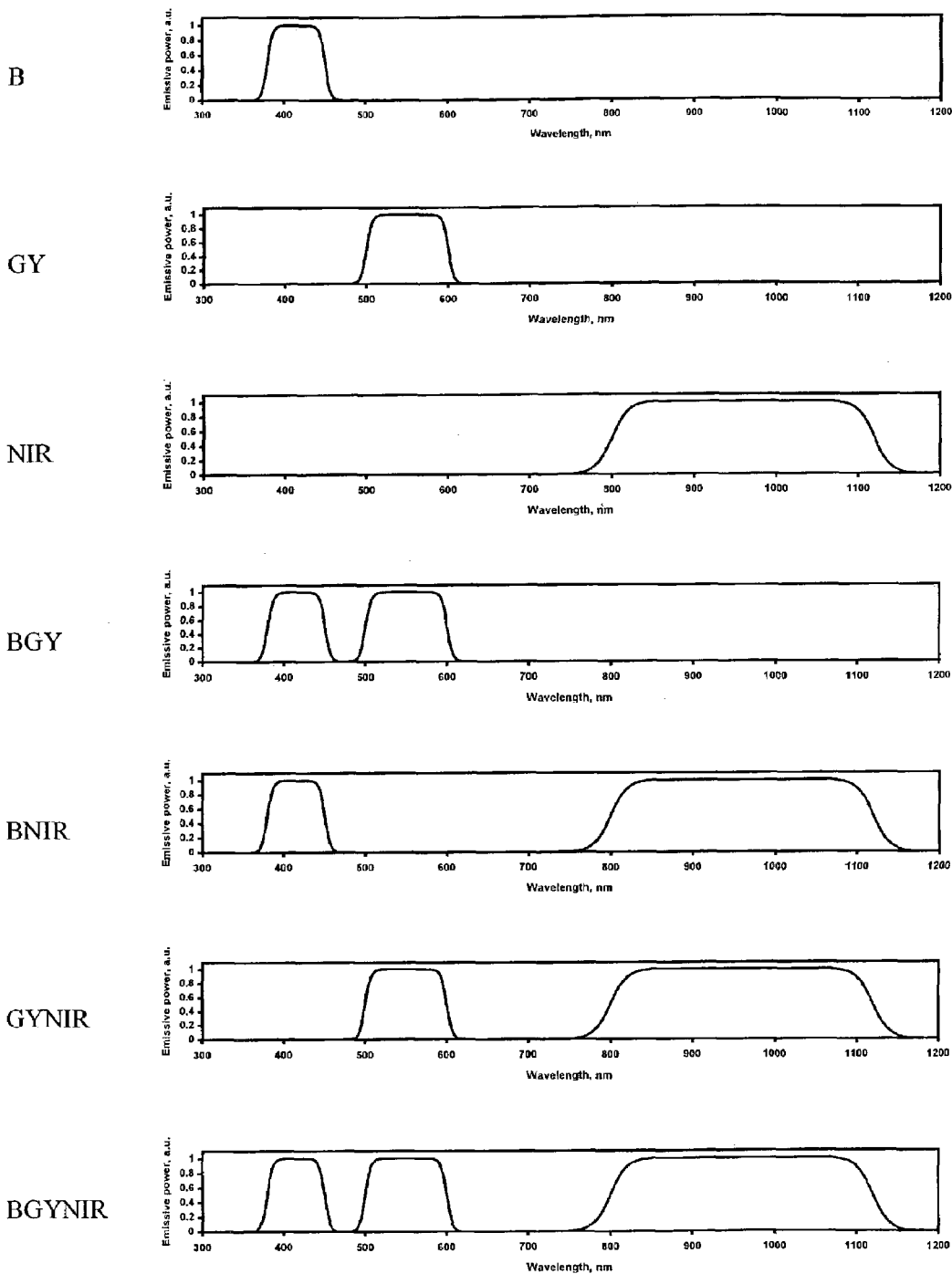
FIG. 7 is a representation of the pass bands for the various filters and filter combinations or output spectrum which may be utilized for treatments in accordance with the teachings of this invention.

In accordance with the first criterion for safe, effective vascular treatment, a broad band lamp spectrum can be filtered to provide one or more of the B, GY, and NIR bands as these bands are defined above. Seven different combinations of these bands are possible: B, GY, NIR, BGY, BNIR, GYNIR, BGYNIR (see FIG. 7).

TABLE 1

Optimal laser wavelengths for vascular treatment

| Type | Vessel Depth, mm | Diameter, mm | Skin type I Spectra, nm | Skin type II Spectra, nm | Skin type III Spectra, nm | Skin type IV Spectra, nm | Skin type V Spectra, nm | Skin type VI Spectra, nm |
|---|---|---|---|---|---|---|---|---|
| Plexus | 0.1 | 0.01 | 400-430 | 405-435 | 405-435 | 410-440 | 410-440 | 410-440 |
| Superficial | 0.25 | 0.25 | 410-440 510-595 | 415-445 510-595 | 415-445 510-595 | 415-445 510-595 | 420-450 540-595 | 420-450 540-595 |
| Intermediate | 0.5 | 0.5 | 510-600 | 510-600 | 530-600 | 530-600 | 530-600 | 530-600 |
| Deep | >1 | >1 | 510-600 800-1100 | 510-600 800-1100 | 530-600 800-1100 | 530-600 850-1100 | 900-1100 | 900-1100 |

Pulsed lasers in these bands, except for the band of 900-1000 nm, have in general very low efficiency (0.1-5%) and high cost.

Figure 6:
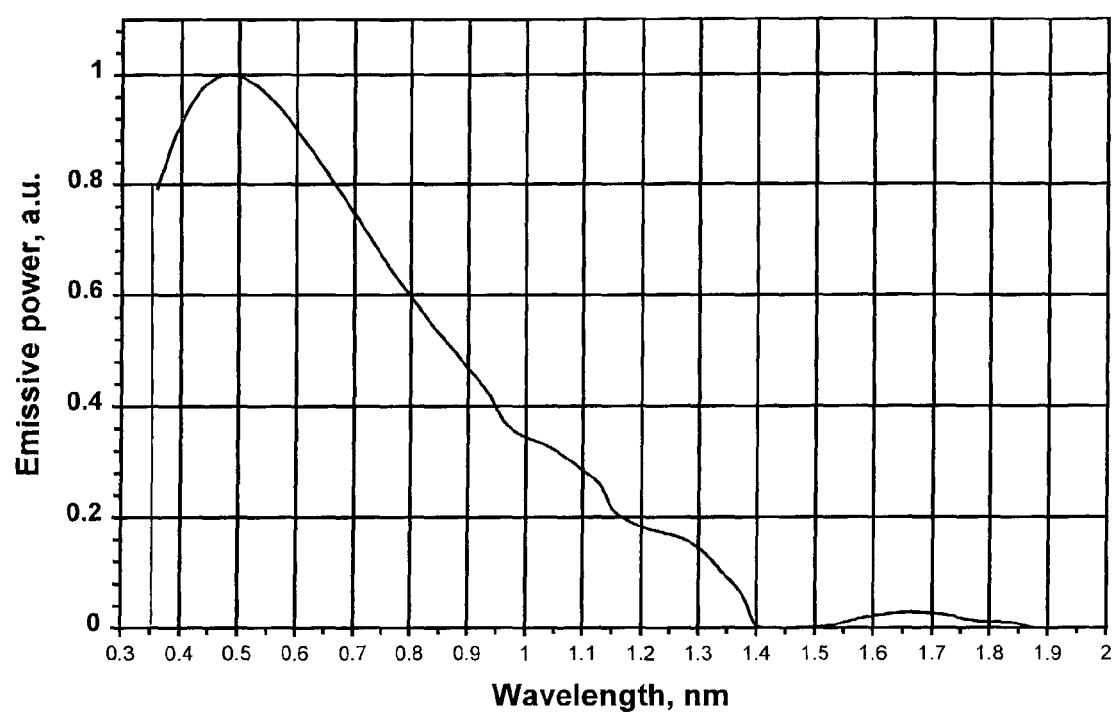
FIG. 6 is a plot of the output spectrum of an Xe flashlamp using a cutoff filter at 360 nm and a water filter of thickness 3 mm.

Alternative light sources can be various types of lamps with proper filtration. Pulsed lamps with high energy have output spectrums which are close to a black body spectrum with certain color temperature. This color temperature can be adjusted by changing current density through the lamp. FIG. 6 shows the spectrum of lamp radiation approximated by the spectrum of blackbody radiation at a temperature of 6000° K.

The second and third criteria depend on physical properties of the filter(s) used. Obviously, no physical filter can have a step-like transmission spectrum. As a result, some tolerance must be allowed in the boundaries between transmission and rejection regions. For example, for the transmission band 500-610 nm, transmission values at ~½ the maximal transmission can be expected at the boundaries of the interval (i.e., 500 nm and 610 nm). Therefore, the actual transmission spectrum at a level of at least 0.1 the maximum value may span from ~480 to ~650 nm. As a rule, the actual output spectrum of the lamp after filtration will be broader than the ideal spectrum. Table 2 shows optimal filtration of a lamp or other broad band light source and optimal color temperature of the lamp/source for treatment of different vascular targets.

TABLE 2

Optimal lamp spectra for vascular treatment

| Vessel | | | Skin type I | | Skin type II | | Skin type III | |
|---|---|---|---|---|---|---|---|---|
| Type | Depth, mm | Diameter, mm | $T_c$, °K. | Spectra | $T_c$, °K. | Spectra | $T_c$, °K. | Spectra |
| Plexus | 0.1 | 0.01 | 6000-8000 | B BGY | 6000-8000 | B BGY | 6000-8000 | B BGY |
| Superficial | 0.25 | 0.25 | 5000-7000 | B BGY BGYNIR | 5000-7000 | B BGY BGYNIR | 5000-7000 | B BGY BGYNIR |
| Intermediate | 0.5 | 0.5 | 4000-6000 | GY GYNIR | 4000-6000 | GY GYNIR | 4000-6000 | GY GNIR |
| Deep | 1 | >1 | 3000-6000 | GYNIR NIR | 3000-6000 | GYNIR NIR | 3000-6000 | GYNIR NIR |

| Vessel | | | Skin type IV | | Skin type V | | Skin type VI | |
|---|---|---|---|---|---|---|---|---|
| Type | Depth, mm | Diameter, mm | $T_c$, °K. | Spectra | $T_c$, °K. | Spectra | $T_c$, °K. | Spectra |
| Plexus | 0.1 | 0.01 | 6000-8000 | B BGY | 6000-8000 | B BGY | 6000-8000 | B BGY |
| Superficial | 0.25 | 0.25 | 5000-6000 | B BGY BGYNIR | 4000-6000 | B GY GYNIR | 4000-6000 | B GY GYNIR |
| Intermediate | 0.5 | 0.5 | 4000-6000 | GY GYNIR | 4000-6000 | GYNIR NIR | 4000-6000 | GYNIR NIR |
| Deep | 1 | >1 | 3000-5500 | NIR GYNIR | 3000-5500 | NIR GYNIR | 3000-4500 | NIR |

Figure 8A:
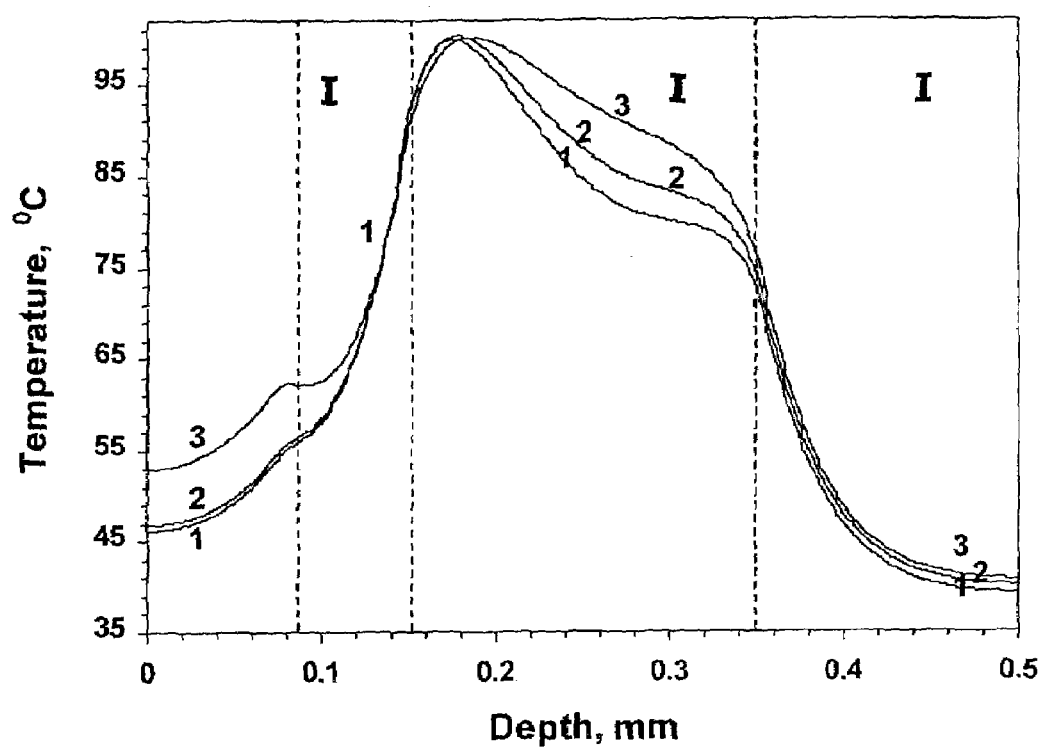
FIGS. 8a and 8b are plots of temperature as a function of depth in the tissue for lamp treatment of superficial and intermediate veins respectively.
Figure 8B:
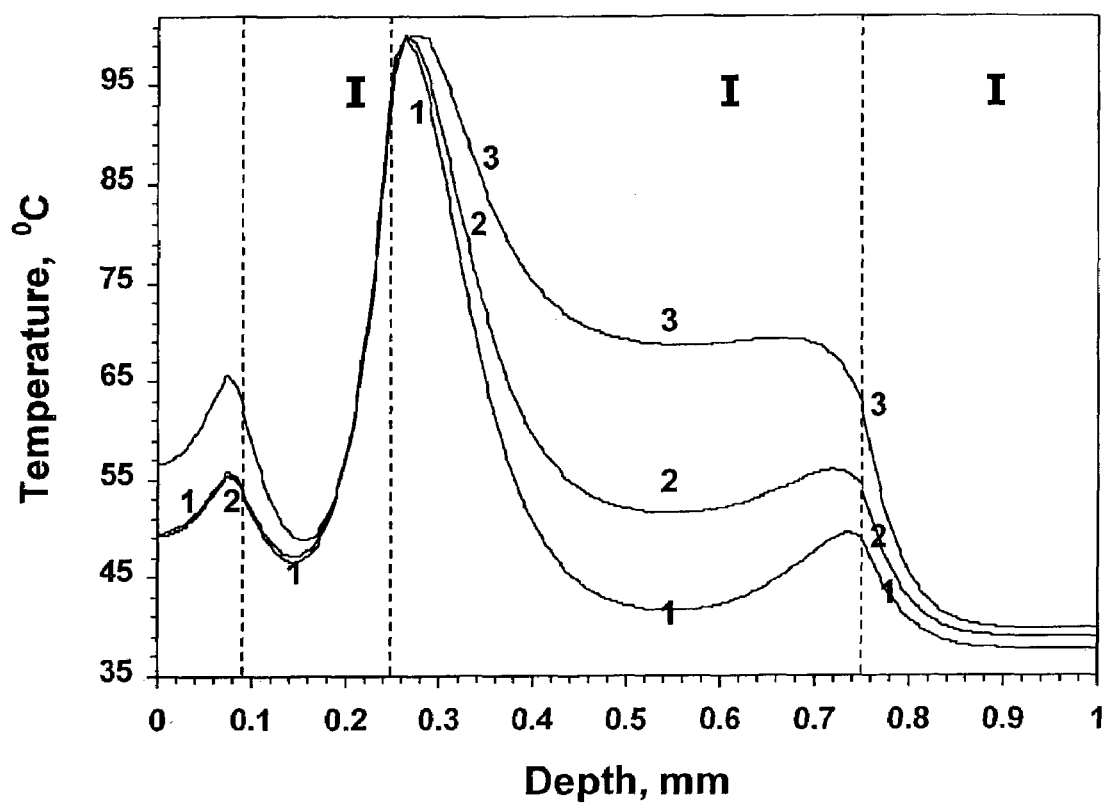

The importance of the concepts of the present invention on temperature is illustrated in FIG. 8 where the effect on the skin for a lamp with different filtration is shown. More specifically, FIG. 8 shows calculated tissue temperature against depth for lamp treatment of superficial (a) and intermediate (b) veins in type II skin. Specifically, plots 1, 2, and 3 are the vertical temperature profiles in the epidermis (I), dermis (II), and blood (III) using GY, GYNIR, and full (F) spectrum filters, respectively. Here, F is a pass band filter with short wavelength cutoff at 500 nm and long wavelength cutoff at 1120 nm. The incident light is a plane wave infinite in the transverse direction. A rectangular light pulse of duration 20 ms is assumed. In all cases, the input light flux is chosen to provide a maximum blood temperature of 100° C. Therefore, various complex phenomena appearing in biotissues at temperatures above the boiling temperature of water need not be considered.

The pass band of the F filter is obtained from that of the GYNIR filter by including the additional spectral range from 610 to 850 nm. Light from the latter range exhibits weak absorption in the dermis, but penetrates deeply therein. However, the contribution of this spectral range to the total heat source density in the blood is expected to be rather small due to the weak absorption. Contrary to this, light from the same range is strongly absorbed by the epidermal melanin, increasing the risk of epidermal injury. Therefore, the F filter is close to the GYNIR filter in treatment efficiency, but is much worse (1.5 times) than both GY and GYNIR from the point of view of the safety.

The simulation results shown in FIG. 8 support the above assumption. For the superficial vein (a), approximately, 4, 8, and 12.5 J/cm² of light energy are needed to heat the blood to the prescribed temperature using the GY, GNIR, and F filters, respectively. The blood temperature is the same for all the filters because almost all of the blood heating is accomplished by the same portion of the spectrum in all cases, even though the available spectrum is different for the various filters; however, the temperature effect on the epidermis is about 1.5 times larger for the F filter than for the G and GNIR filters. The same conclusions hold for the intermediate vein, although the required light fluxes are somewhat smaller, being 3.5, 6.7, and 10.5 J/cm² for the G, GNIR, and F filters respectively. The temperature effect on the epidermis is, however, substantially the same for the G and GNIR filters.

To choose the best filter for a particular treatment, one needs to take into account that irreversible vein occlusion proceeds through the thermal coagulation of the whole vessel endothelium, including its bottommost part. However, overheating of the topmost part of the vessel wall may disrupt the vessel, leading to purpura. The GYNIR and F filters provide less risk of purpura than the GY filter, providing a more uniform heating of the vein wall. The distinction in heating uniformity is rather small for the superficial vessels, but becomes appreciable with increasing vessel diameter. However, as already mentioned, the GY and GYNIR filters require less energy and decrease the risk of the epidermal injury compared to the F filter. Finally, using the GYNIR filter instead of the GY filter increases treatment efficiency since the GYNIR pass band is wider and, therefore, less light energy is filtered out.

All filters that transmit or block a part of the spectrum selectively, and are therefore suitable for obtaining the wavelength bands indicated above, can be based on one of four mechanisms: absorption, interference, birefringence or scattering. In addition, fluorescence of one or more components of, for example, an absorption filter can be used advantageously.

In absorption filters, the unwanted regions of the spectrum are absorbed and their energy (excluding fluorescence conversion) is usually converted into heat. Such filters are based on glass, crystals, solutions, gelatin, or plastic containing substances with selective absorption materials such as transition metal ions ($Co^{+2}$, $Co^{+3}$, $Ni^{+2}$, $Ti^{+3}$, $Cu^{+2}$, $V^{+3}$, $V^{+4}$, $Mn^{+2}$, $Mn^{+3}$, $Cr^{+2}$, $Cr^{+3}$ etc.), organic colorants (luminescent and non-luminescent dyes of different origin), charge transfer systems (for example solutions of $CuSO_4*5H_2O$, $NiSO_4*6H_2O$, $CoSO_4*6H_2O$ or $K_2CrO_4$ with ligand ions such as ammonia, water, acetate etc), bandgap materials ($CdS_{1-x}:Se_x$, CdS, GaP etc.), colloidal metals (Au, Ag, Cu), or the color centers.

The best NIR or long-pass filters with wavelengths shorter than approximately 800-900 nm cut are based on thermally processed $CdS_{1-x}Se_x$-doped glass, glass with colloidal Au or liquid or plastic or gel, porous glass or porous transparent ceramic doped with dye.

The best visible band-pass filters for blue Band green GY light are based on a combination of glasses doped with transition metals ($Cu^{+2}$, $Ti^{+3}$, $Fe^{+2}$, $Co^{+2}$, $Co^{+3}$) and/or solutions of some metal salts with proper ligands (chelats) in liquid or solid matrix. Other ways to build blue and green-yellow filters are to use solutions or plastics or quartz microspores, glass or sol gel doped with dyes. Absorptive filters are the best in terms of sharpness of transmission boundaries.

In scattering filters (Christiansen filters), glass (crystal) powder is suspended in a two-phase compound (liquid/solid, liquid crystal/solid state) with matching refractive index at a certain wavelength and different wavelength dispersion of the refractive index for the two phases. A cuvette filled with such a substance is transparent at a chosen wavelength and scatters at other wavelengths because of refractive index mismatch. Since most liquids or liquid crystals have a stronger variation of refractive index with temperature than do solids, varying the temperature of the composition can be used for spectral tuning of the transmission curve.

Interference filters (IF) are formed of a sandwich of materials, for example SiO2, TiO2, which have different refractive indices so that a reflection of a different wavelength is obtained from each layer. The pass-band is of the wavelength (s) which are not reflected by any of the layers. IF provides a relatively sharp cut-off, sharper than that of absorption filters for a given incident angle. One drawback is that the transmission spectrum of IF strongly depends on the incident angle of a beam. A lamp has a very wide (360 deg) angular spectrum. Because of that, the border of the output wavelength spectra after IF is significantly wider than after a good absorption filter. To minimize this effect IF should be located at a place in the apparatus used where angular distribution is narrowest, for example on the surface of lamp envelope or on the surface of the tube surrounded the lamp envelope.

Other groups of filters are based on different approaches, such as acousto-optic tunable filters, liquid crystal filters, and filters based on color-selective absorption by surface plasmon at a metal-dielectric interface.

Table 3provides examples of suitable filter materials for the seven different wavelength band combinations indicated above.

| FILTER/ SUBSTANCE | NONORGANIC | ORGANIC |
|---|---|---|
| BLUE (B) FILTER | $Co^{2+}$ and/or $Cu^{2+}$ ionically doped glass ($BG12^1$) $CuSO_4$, $CoCl_2$ solutions with ionically doped glass | STYRYL $6^4$ (solvent, plastic, porous glass) |
| GREEN (GY) FILTER | $Cr^{3+}$ and/or $Fe^{2+}$ ionically doped glass ($BG8^2$, $LB6^3$) | $DASPI^4 + DNTTCI^4$ (solvent, plastic, porous glass) |

-continued

| FILTER/ SUBSTANCE | NONORGANIC | ORGANIC |
|---|---|---|
| NEAR INFRARED (NIR) FILTER | $NiSO_4$ solution with ionically doped glass $CdS_{1-x}:Se_x$, colloidally doped glasses ($RG730^1$) | STYRYL $9M^4$ (solvent, plastic, porous glass) Commercial azo dyes |
| BGY FILTER | $Cu^{2+}:Fe^{2+}$ ionically doped glass ($BG26^1$, $BG40^1 + GG375^1$) $CuSO_4$ solution | $DNTTCI^4$ (solvent, plastic, porous glass) |
| BNIR FILTER | $Ni^{2+}:CO^{2+}$ doped glass ($BG3^1$, $BGG20^2$, $QB19^3$) | $DASBTI^4$ (solvent, plastic, porous glass) |
| GYNIR FILTER | Transient metals ionically doped glass ($LB16^3 + CB535^3$) | $DASPI^4$ (solvent, plastic, porous glass) |
| BGYNIR FILTER | Transient metals ionically doped glass ($LB16^3$) | Combination of the dyes |

A filter or combinations of filters can be implemented in different locations along the optical path including, for a lamp as shown in FIG. 1:

1. Coating or material of reflector 38;
2. Material or coating of lamp's envelope;
3. Cooling liquid of the lamp which may be doped by absorption and/or fluorescence particles;
4. Tube 42 surrounding the lamp doped or coated by filtering material;
5. Material or coating on a waveguide or other output component 40;
6. Lotion applied to the patient's skin with the function of reflecting, scattering or absorpting unwanted radiation wavelengths.

A filter can also be built as an angular dispersion element (e.g., prism, grating). In this case, the radiation beam at the skin surface has a different spectrum (color) at different locations on the surface. Such a beam is referred to as a rainbow beam. Output spectrum can be adjusted by tuning the aperture of the output beam.

In the past it was believed that blue light, generally in the preferred range of this invention from 380-450 nm, could not be used in optical radiation dermatology because melanin was so absorbent at these wavelengths that they were too dangerous. However, as illustrated above, the safety ratio at these wavelengths makes it feasible to use these wavelengths for treating shallow blood vessels since the vessels absorb so much more strongly at these wavelengths than at other wavelengths, the energy of the applied radiation may be two to six times less than that for conventional treatments, thereby minimizing epidermal damage while still achieving the desired temperature rise in the blood vessels.

Further, in accordance with the teachings of this invention, pressure may be utilized to control the depth at which treatment occurs. Thus, if mild pressure is applied to the treatment area, blood will be forced out of the blood vessels in the plexus area, resulting in greater energy absorption at the deeper spider veins, which would be the treatment target, and improving the safety ratio If the pressure is applied to surround the treatment area, blood will be forced into and/or held in the blood vessels in the treatment area, resulting greater energy absorption at the superficial vessels and better treatment of this target. For deeper vessels, additional pressure may be applied to remove blood from the vessels overlying the vessel on which treatment is desired to enhance the safety ratio for such treatment. Cooling may also be utilized to remove blood from upper vessels, particularly plexus vessels.

In addition to treatment for removing spider veins or other shallow vascular lesions, the teachings of this invention may also be used to treat port wine stain by destroying the blood vessels causing this condition, and psoriasis by destroying the vascularization in the plexus area which supports the psoriasis plaque, as well as rosacea, telagiecasia, and hemangioma by similar mechanisms in the plexus area. Further, by heating blood vessels of the papillary dermis in general, and the plexus in particular, tissue in the area of these vessels may be heated, for example to approximately 60-70° C. The perturbing of these blood vessels stimulates fibroblasts to be produced, facilitating the growth of new collagen in this area, and thus the removal of wrinkles, scars and other skin blemishes. Heating of the superficial, intermediate and deep veins may also be utilized to either treat the veins themselves, for example to remove the veins, or to heat surrounding tissue to effect some other desired treatment. For example, in addition to treatment of vascular lesions, blood in the vessels can be used as a chromophore for treatment of problems associated with other organs/body components. Rapidly proliferating cells in organs such as hair follicles, sebaceous follicles or glands, pigmented lesions, epidermis, nails and tumors need adequate blood supply, which is provided by well developed vascular systems. Causing damage to the blood supply system or inducing heat diffusion from vessels to the surrounding tissue can trigger other mechanisms to treat such an organ. Superficial and deep arteriovenuos plexuses can be targeted for treatment of skin texture and wrinkles. Heating of vessels in plexuses can cause an inflammatory reaction of surrounding tissue and stimulate influx of fibroblasts for collagen production. As a result, skin texture, wrinkles, and dermishypodermis junction and elasticity of skin can be improved. Cellulite can also be reduced by artefiovenuos plexus treatment. Highly vasculated muscular tissue can be treated using the techniques of the present invention in areas of the body with thin skin, particularly above subcutaneous regions (face, neck). As a result, skin lifting and deep wrinkle improvement can be achieved. So, the present invention, in addition to vascular lesion treatment, can be used for hair growth management (reduction and stimulation), acne reduction and prevention, pigmented lesion treatment, skin texture and wrinkles improvement, skin elasticity improvement, cellulite reduction, nail disease treatment, cutaneous tumor treatment, skin lifting, odor production reduction etc.

The spot size for treatments employing the teachings of this invention are preferably small, for example in the range between 0.1-1 cm for a laser and 0.1-5 cm for a lamp for vessels at a depth of approximately 1 mm or less, and somewhat larger for deeper vessels. Where blood vessels are being treated, this small spot size can be applied at selected points along the blood vessel to destroy the vessel rather than over the entire vessel, clotting at several points along the vessel normally being sufficient to destroy the vessel.

The relationship of pulsewidth $\tau$ to thermal relaxation time (TRT) of the vessels should be in the range:

$$0.1 TRT < \tau < 100 TRT.$$

Power and fluence should be sufficient to heat blood in the vessels to a temperature of 50-100C.

While the invention has been particularly shown and described above with reference to preferred embodiments, the foregoing and other changes in form and detail may be made therein by one skilled in the art while still remaining within the spirit and scope of the invention which is to be defined only by the appended claims.

What is claimed is:

1. A method for performing dermatological treatments on blood vessels at depths of less than about 0.5 mm by applying optical radiation through skin to a treatment area which includes substantial radiation having a safety ratio of approximately at least one in a blue wavelength band of approximately 380-450 nm to induce coagulation at a target blood vessel.

2. A method as claimed in claim 1 wherein the optical radiation is coherent radiation and is of a wavelength in a range of approximately 400-450 nm.

3. A method as claimed in claim 2 wherein the wavelength of the coherent optical radiation is approximately 420-440 nm.

4. A method as claimed in claim 1 wherein the optical radiation is non-coherent broadband radiation, and wherein the blue radiation is in a band from 380-450 nm.

5. A method as claimed in claim 1 including applying pressure to a patient's skin to remove blood from blood vessels in an area of treatment above blood vessels for which treatment is desired.

6. A method as claimed in claim 1 including cooling a patient's skin above an area of treatment.

7. A method for performing treatments involving blood vessels by:
providing a broad-band optical radiation source,
filtering radiation from said source to pass only wavelengths from said source providing a safety ratio which is approximately at least one, wherein said filtered radiation comprises at least two substantially separate wavelengths of light from distinct bands of radiation selected from the group consisting of at least one wavelength in a blue wavelength band of approximately 380-450 nm, at least one wavelength in a green-yellow wavelength band of approximately 500-610 nm, and at least one wavelength in an NIR band of approximately 800-1120 nm, and
applying filtered radiation from said source through skin to the blood vessels involved in the treatment.

8. A method as claimed in claim 7 wherein radiation filtered from said source includes radiation having a wavelength from approximately 610 nm to 800 nm.

9. A method as claimed in claim 7 wherein radiation filtered from said source includes radiation having a wavelength from approximately 610 nm to 900 nm.

10. A method as claimed in claim 7 wherein radiation filtered from said source includes radiation having a wavelength from approximately 450 nm to 500 nm.

11. A method as claimed in claim 7 wherein radiation filtered from said source includes radiation having a wavelength longer than 1120nm.

12. A method as claimed in claim 7 including cooling a patient's skin above an area of treatment.

13. A method as claimed in claim 7 wherein the filtered radiation passed during said filtering step further includes radiation in a green-yellow wavelength band, wherein radiation between said blue band and said green-yellow band being filtered out.

14. A method as claimed in claim 7 wherein radiation passed during said filtering step includes radiation in an NIR wavelength band, radiation between said blue band, said green-yellow band and said NIR band being filtered out.

15. A method as claimed in claim 7 wherein radiation passed during said filtering step includes radiation in a blue wavelength band and radiation in an NIR wavelength band, at least some radiation between said bands being filtered out.

16. A method as claimed in claim 7 wherein radiation passed during said filtering step further includes radiation in a green-yellow wavelength band and radiation in an NIR wavelength band, radiation between said bands being filtered out.

17. Apparatus for performing dermatological treatments involving blood vessels including:
a broad-band optical radiation source;
a mechanism for filtering radiation from said source to pass only wavelengths from said source providing a safety ratio which is approximately at least one, wherein the mechanism for filtering is capable of passing at least two substantially separate wavelengths of light from distinct bands of radiation, wherein the wavelength bands are selected from the group consisting of at least one wavelength in a blue wavelength band of approximately 380-450 nm, at least one wavelength in a green-yellow wavelength band of approximately 500-610 nm, and at least one wavelength in an NIR wavelength band of approximately 800-1120 nm; and
a mechanism for applying filtered radiation from said source to the blood vessels involved in the treatment.

18. Apparatus as claimed in claim 17 wherein radiation filtered from said source by said mechanism for filtering includes radiation having a wavelength from approximately 610 nm to 800 nm.

19. Apparatus as claimed in claim 17 wherein radiation filtered from said source by said mechanism for filtering includes radiation having a wavelength from approximately 610 nm to 900 nm.

20. Apparatus as claimed in claim 17 wherein radiation filtered from said source by said filtering means includes radiation having a wavelength from approximately 450 nm to 500 nm.

21. Apparatus as claimed in claim 17 including a mechanism for applying pressure to a patient's skin to remove blood from blood vessels in an area of treatment above blood vessels for which treatment is desired.

22. Apparatus as claimed in claim 17 including a mechanism for cooling a patient's skin above an area of treatment.

23. Apparatus s claimed in claim 17 wherein radiation passed by said mechanism for filtering includes radiation in a blue wavelength band and radiation in a green-yellow wavelength band, radiation between said bands being filtered out.

24. Apparatus as claimed in claim 23 wherein radiation passed by said mechanism for filtering includes radiation in an NIR wavelength band, radiation between said green band and said NIR band being filtered out.

25. Apparatus as claimed in claim 17 wherein radiation passed by said mechanism for filtering includes radiation in a blue wavelength band and radiation in an near-infrared wavelength band, at least some radiation between said bands being filtered out.

26. Apparatus as claimed in claim 17 wherein radiation passed by said mechanism for filtering includes radiation in a green-yellow wavelength band and radiation in an near infrared wavelength band, radiation between said bands being filtered out.

27. A method for performing treatments involving blood vessels at depths of less than about 0.5 mm by:
providing a broad-band optical radiation source,
filtering radiation from said source to pass only wavelengths from said source providing a safety ratio which is approximately at least one, wherein the filtered wavelengths are within a blue wavelength band of approximately 380-450 nm,
applying pressure to a patient's skin to remove blood from blood vessels in an area of treatment above blood vessels for which treatment is desired, and
applying the filtered radiation from said source through skin to the blood vessels involved in the treatment.

28. A method for performing dermatological treatments involving at least one of plexus blood vessels and superficial blood vessels by applying optical radiation to a treatment area which includes substantial radiation in a blue wavelength band of approximately 380-450 nm and applying a second band of optical radiation to the treatment area, wherein the second band comprises a green-yellow wavelength band of approximately 510-595 nm.

29. A method for performing dermatological treatments involving at least one of plexus blood vessels and superficial blood vessels by applying optical radiation to a treatment area which includes substantial radiation in a blue wavelength band of approximately 380-450 nm and applying a second band of optical radiation, wherein the second band comprises radiation of approximately 500-610 nm in a green-yellow band.

30. A method for performing dermatological treatments involving at least one of plexus blood vessels and superficial blood vessels by applying optical radiation to a treatment area which includes substantial radiation in a blue wavelength band of approximately 380-450 nm, applying a second band of optical radiation, wherein the second band comprises radiation of approximately 500-610 nm in a green-yellow band, and applying a third band of optical radiation, wherein the third band comprises radiation in an NIR band.

31. A method for performing treatments on blood vessels by:
providing a broad-band optical radiation source,
filtering radiation from said source to pass only selected wavelengths from said source which are in at least two separate bands, the bands selected from the group of a blue band of approximately 380-450 nm, a green-yellow band of approximately 500-610 nm, and a near infrared (NIR) band of approximately 800-1120 nm, at least some of the radiation in wavelengths between the passed radiation bands being filtered out, and
applying filtered radiation from the at least two bands, sequentially or simultaneously, through skin to the blood vessels involved in the treatment.

32. A method as claimed in claim 31 wherein radiation from all three of said bands are passed during said filtering step.

33. A method for performing treatments on veins by:
providing a broad-band optical radiation source,
filtering radiation from said source to pass only selected wavelengths from said source, wherein the selected wavelengths are selected from the group consisting of at least one wavelength in a blue wavelength band of approximately 380-450 nm, at least one wavelength in a green-yellow wavelength band of approximately 500-610 nm, and at least one wavelength in an MR band of approximately 800-1120 nm, the wavelengths and duration of the radiation being selected to provide substantially uniform heating of each vessel and to provide a safety ratio which is approximately at least one, and
applying filtered radiation from the blue, green-yellow or NIR bands, either sequentially or simultaneously, to the vessel involved in the treatment.

34. A method as claimed in claim 33 wherein radiation passed during said filtering step includes radiation in a green-yellow wavelength band and radiation in an NIR wavelength band, radiation between said bands being filtered out.

35. A method as claimed in claim 33 wherein the pulse duration is approximately 0.1 to 100 times the thermal relaxation time of the vessel involved in the treatment.

36. Apparatus for performing dermatological treatments on blood vessels including:
   a broad-band optical radiation source;
   a mechanism for filtering radiation from said source to pass only selected wavelengths from said source which are in at least two separate bands, the bands selected from the group of a blue band of approximately 380-450 nm, a green-yellow band of approximately 500-610 nm, and a near infrared (NIR) band of approximately 800-1120 nm, at least some of the radiation in wavelengths between the passed radiation bands being filtered out; and
   a mechanism for applying filtered radiation from the at least two bands, sequentially or simultaneously, to the blood vessels involved in the treatment.

37. Apparatus as claimed in claim 36 wherein said mechanism for filtering passes radiation from all three of said bands.

38. Apparatus for performing dermatological treatments on blood vessels including:
   a broad-band optical radiation source providing pulses of a selected duration;
   a mechanism for filtering radiation from said source to pass only selected wavelengths from said source, the wavelengths and duration of the radiation being selected to provide substantially uniform heating of each vessel wherein the wavelengths are selected from the group consisting of at least one wavelength in a blue wavelength band of approximately 380-450 nm, at least one wavelength in a green-yellow wavelength band of approximately 500-610 nm, and at least one wavelength in an NIR band of approximately 800-1120 nm; and
   a mechanism for applying filtered radiation from the wavelength bands, sequentially or simultaneously, to the vessels involved in the treatment.

39. Apparatus as claimed in claim 38 wherein radiation passed by said mechanism for filtering includes radiation in a green-yellow wavelength band and radiation in an NIR wavelength band, radiation between said bands being filtered out.

40. Apparatus as claimed in claim 38 wherein the pulse duration provided by said source is approximately 0.1 to 100 times the thermal relaxation time of the vessel involved in the treatment.

* * * * *